(12) United States Patent
Goeke et al.

(10) Patent No.: US 6,579,851 B2
(45) Date of Patent: Jun. 17, 2003

(54) EFFECTS OF GLUCAGON-LIKE PEPTIDE-1 (7-36) ON ANTRO-PYLORO-DUODENAL MOTILITY

(75) Inventors: Burkhard Goeke, Gauting (DE); Joerg Schirra, Kirchhain (DE)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/805,507

(22) Filed: Mar. 14, 2001

(65) Prior Publication Data

US 2002/0098195 A1 Jul. 25, 2002

Related U.S. Application Data

(60) Provisional application No. 60/189,091, filed on Mar. 14, 2000.

(51) Int. Cl.[7] .............................................. A61K 38/26
(52) U.S. Cl. ......................................................... 514/12
(58) Field of Search ........................................... 514/12

(56) References Cited

FOREIGN PATENT DOCUMENTS

| WO | 98/39022 | 9/1998 |
|---|---|---|
| WO | 99/64060 | 12/1999 |

OTHER PUBLICATIONS

Schirra et al., "Gastric–Emptying and Release of Incretin Hormones After Glucose–Ingestion in Humans" (Jan. 1, 1996) Journal Of Clinical Investigation, 97(1),92–103.*
Schirra et al., "Mechanisms of the Antidiabetic Action of Subcutaneous Glucagon–like Peptide–1(7–36) Amide in Non–Insulin Dependent Diabetes Mellitus" (1998) J. Endocrinol., 156, 177–185.*
Aros et al., "Effetos del Glucagón–like Peptide–1 (GLP–1) en la Acomodación Y Vaciado Y la Saciedad en Humanos" (Jun. 16–20, 2001) XXVIII Congreso Nacional de la Sociedad Española de Patologia Digestiva, accessed Oct. 4, 2002 at http://www.congressreview.co.*
Anvari et al., "Effects of GLP–1 on Gastric Emptying, Antropyloric Motility, and Transpyloric Flow in Response to a Nonnutrient Liquid," Digestive Diseases and Sciences 43(6):1133–1140 (1998).
Anvari et al., "Effect of GLP–1 on Gastric Emptying, Antropyloric Motility, Transpyloric Flow and Gastric Emptying of Non–nutrient Liquids in Conscious Dogs," Gastroenterology 108(4 Suppl.):A563 (1995).
Anvari et al., "Sites of Action of GLP–1 to Inhibit Transpyloric Flow and Gastric Emptying of Non–nutrient Liquids in Conscious Dogs," Clinical and Investigative Medicine 18(4 Suppl.):B56 (1995).
Chang et al., "A Randomized Study Comparing Glucagon and Hyoscine N–butyl Bromide Before Endoscopic Retrograde Cholangiopancreatography," Scandinavian Journal of Gastroenterology 30(3):283–286 (1995).
Giralt et al., "Sympathetic Pathways Mediate GLP–1 Actions in the Gastrointestinal Tract of the Rat," Regulatory Peptides 74(1):19–25 (1998).

Moses et al., "Suppression of Duodenal Motility During ERCP by L–Hyoscyamine Versus Glucagon: A Randomized Prospective, Double Blinded Trial," Gastroenterology 114(4 Part 2):A533 (1998).
Näslund et al., "Distal Small Bowel Hormones: Correlation with Fasting Antroduodenal Motility and Gastric Emptying," Digestive Diseases and Sciences 43(5):945–952 (1998).
Nauck, "Is Glucagon–like Peptide 1 an Incretin Hormone?," Diabetologia 42(3):373–379 (1999).
Quigley, "Gastroduodenal Motility," Current Opinion in Gastroenterology, 15(6):481–491 (1999).
Qvigstad et al., "Comparison of Glucagon Atropine and Placebo as Pre Medication for Endoscopy of the Upper Gastro Intestinal Tract," Scandinavian Journal of Gastroenterology, Database Accession No. PREV197968075464, Abstract (1979).
Schirra et al., "Differential Effects of Subcutaneous GLP–1 on Gastric Emptying, Insulin Release and Exocrine Pancreatic Secretion in Man," Gastroenterology 108(4):A1003 (1995).
Schirra et al., "Effects of GLP–1 on Human Antro Pyloro–duodenal Motility," Gastroenterology 110(4):A1116 (1996).
Schirra et al., "Effects of Glucagon–like Peptide–1(7–36) amide on Antro–pyloro–duodenal Motility in the Interdigestive State and With Duodenal Lipid Perfusion in Humans," Gut 46(5):622–631 (2000).
Schirra et al., "Differential Effects of Subcutaneous GLP–1 on Gastric Emptying, Antroduodenal Motility, and Pancreatic Function in Men," Proceedings of the Association of American Physicians 109(1):84–97 (1997).
Schirra et al., "Endogenous GLP–1(7–36) Amide Controls Endocrine Pancreatic Secretion and Antroduodenal Motility in Human," Gastroenterology 114(4 Part 2):A1178 (1998).
Schirra et al., "Effects of GLP–1 on Pyloric Motility and Endocrine Pancreatic Response in the Interdigestive State and with Duodenal Lipid," Gastroenterology 116(4 Part 2):A643 (1999).
Tolessa et al., "Inhibitory Effect of Glucagon–like Peptide–1 on Small Bowel Motility. Fasting but not fed motility inhibited via nitric oxide independently of Insulin and Somatostatin," J. of Clinical Investigation 102(4):764–774 (1998).
Vecht et al., "The Dumping Syndrome. Current Insights into Pathophysiology, Diagnosis and Treatment," Scandinavian Journal of Gastroenterology (Supplement) 223:21–27 REF: 95 (1997).

* cited by examiner

Primary Examiner—Jon P. Weber
(74) Attorney, Agent, or Firm—McKee, Voorhees & Sease, P.L.C.

(57) ABSTRACT

The present invention provides an effective method for inhibiting antro-duodenal motility in healthy subjects and patients suffering from various disorders, without the side effects associated with other pharmaceutical compositions. GLP1(7–36)amide slows antro-duodenal motility and may be used for the treatment or prevention of gastrointestinal disorders such as diarrhea, postoperative dumping syndrome and irritable bowel syndrome, and also premedication in endoscopic procedures.

5 Claims, 10 Drawing Sheets

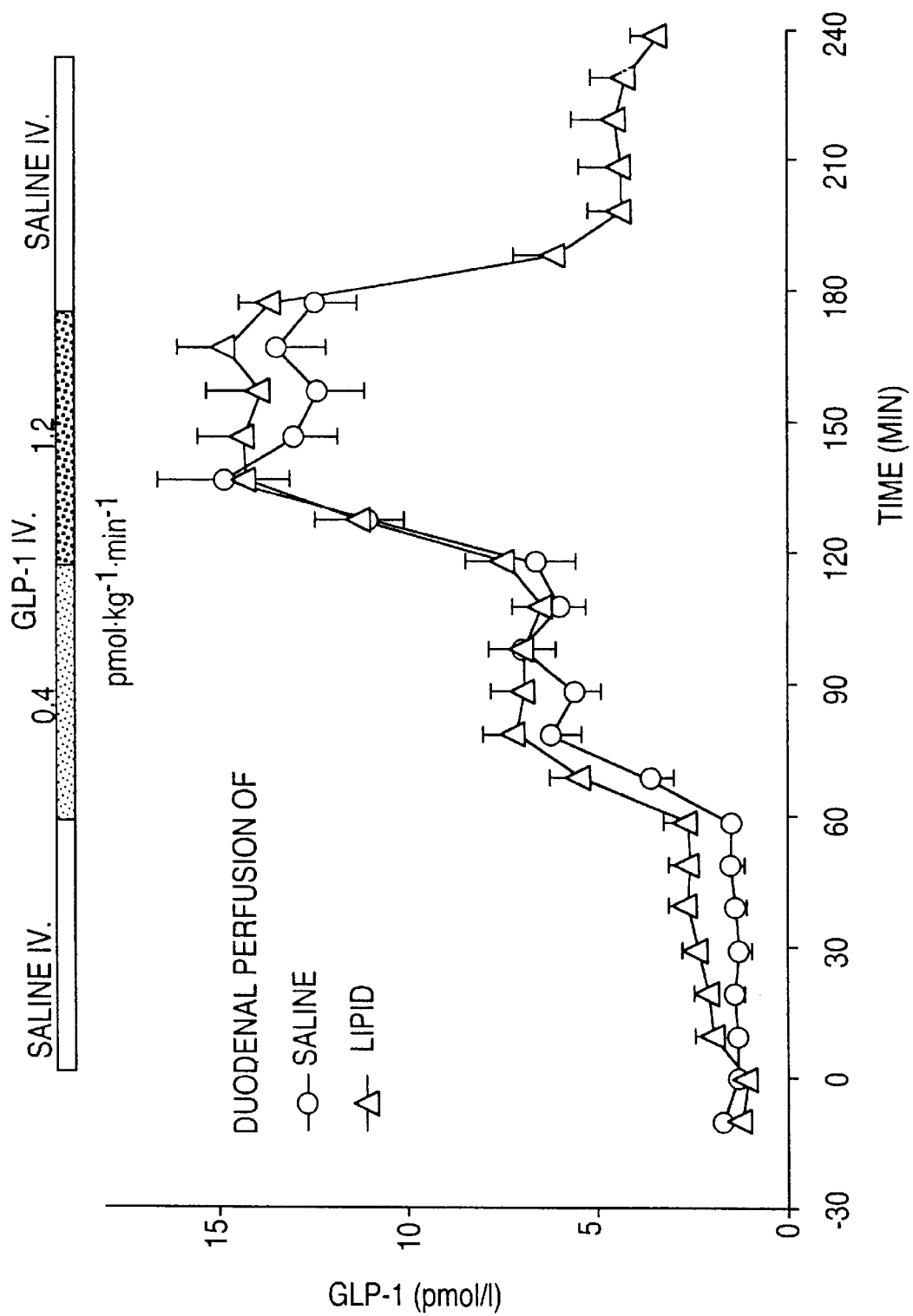

FIG. 2A
INTERDIGESTIVE
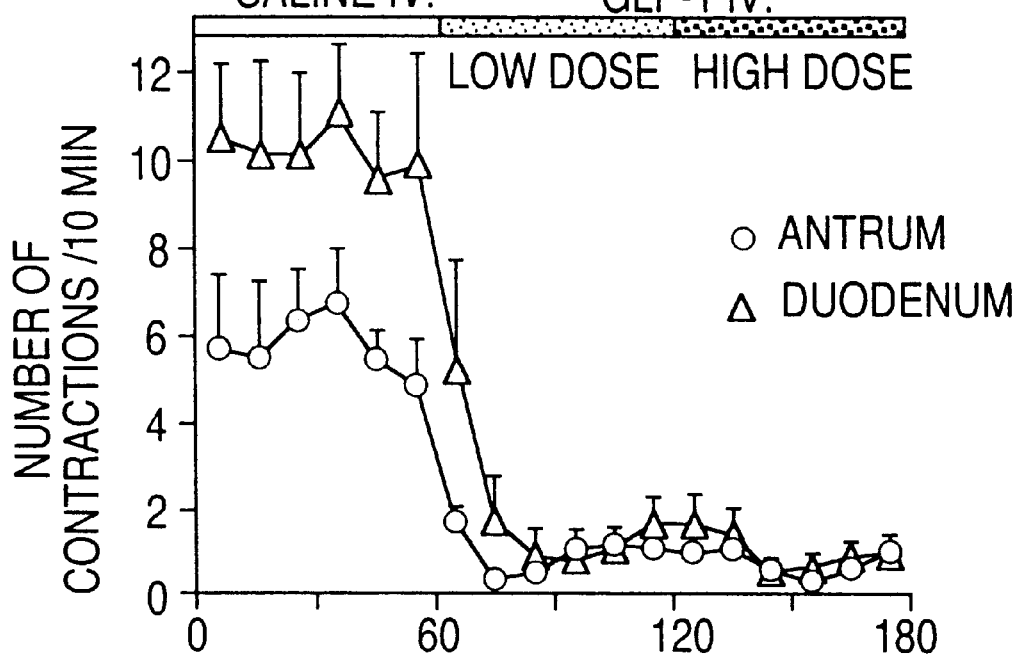
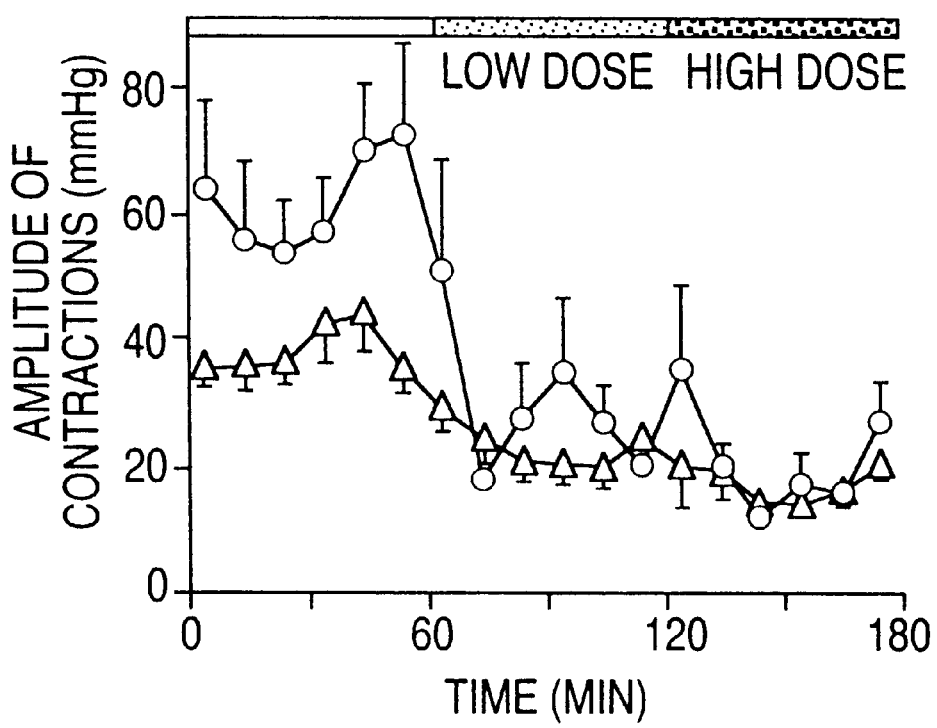

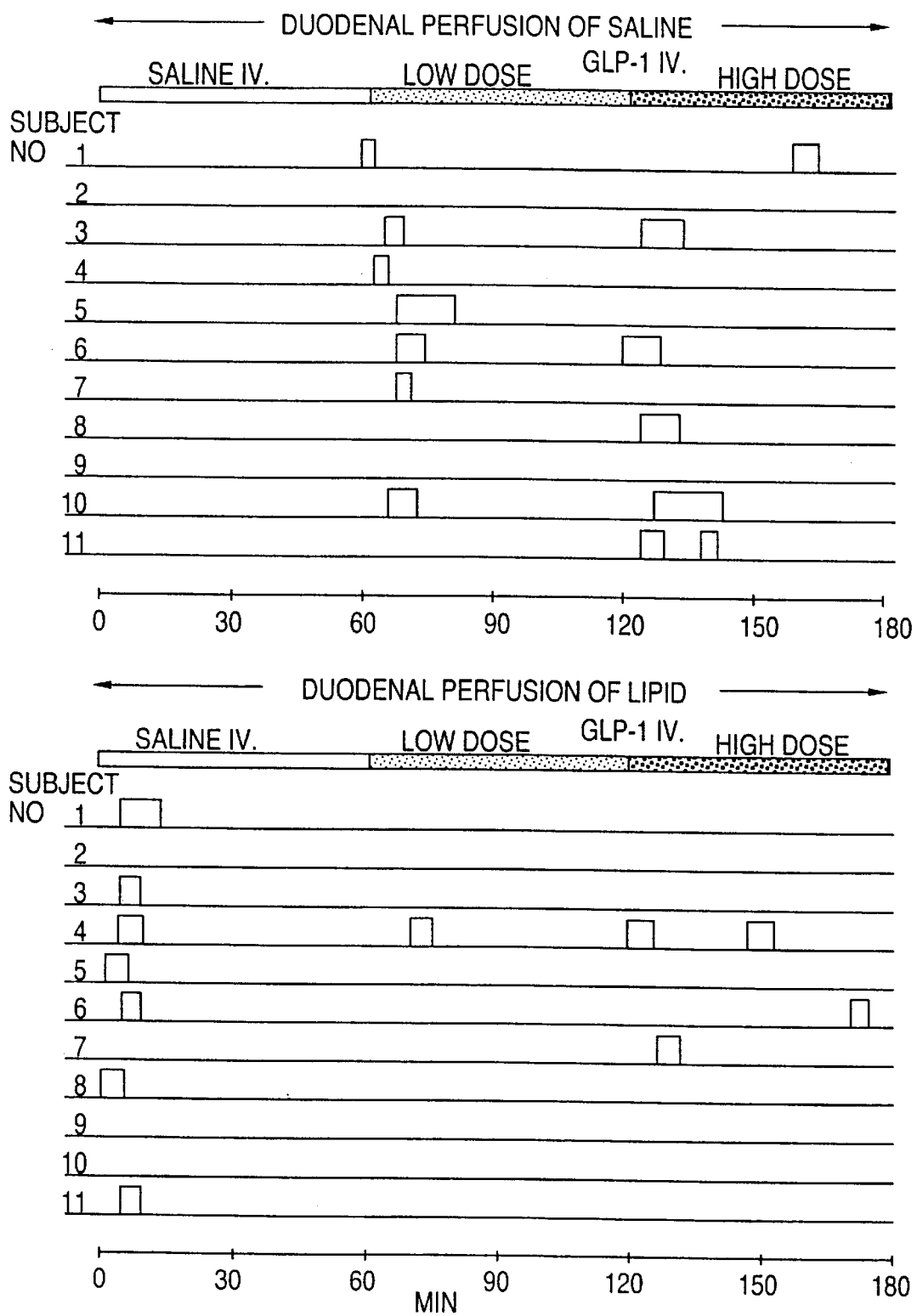

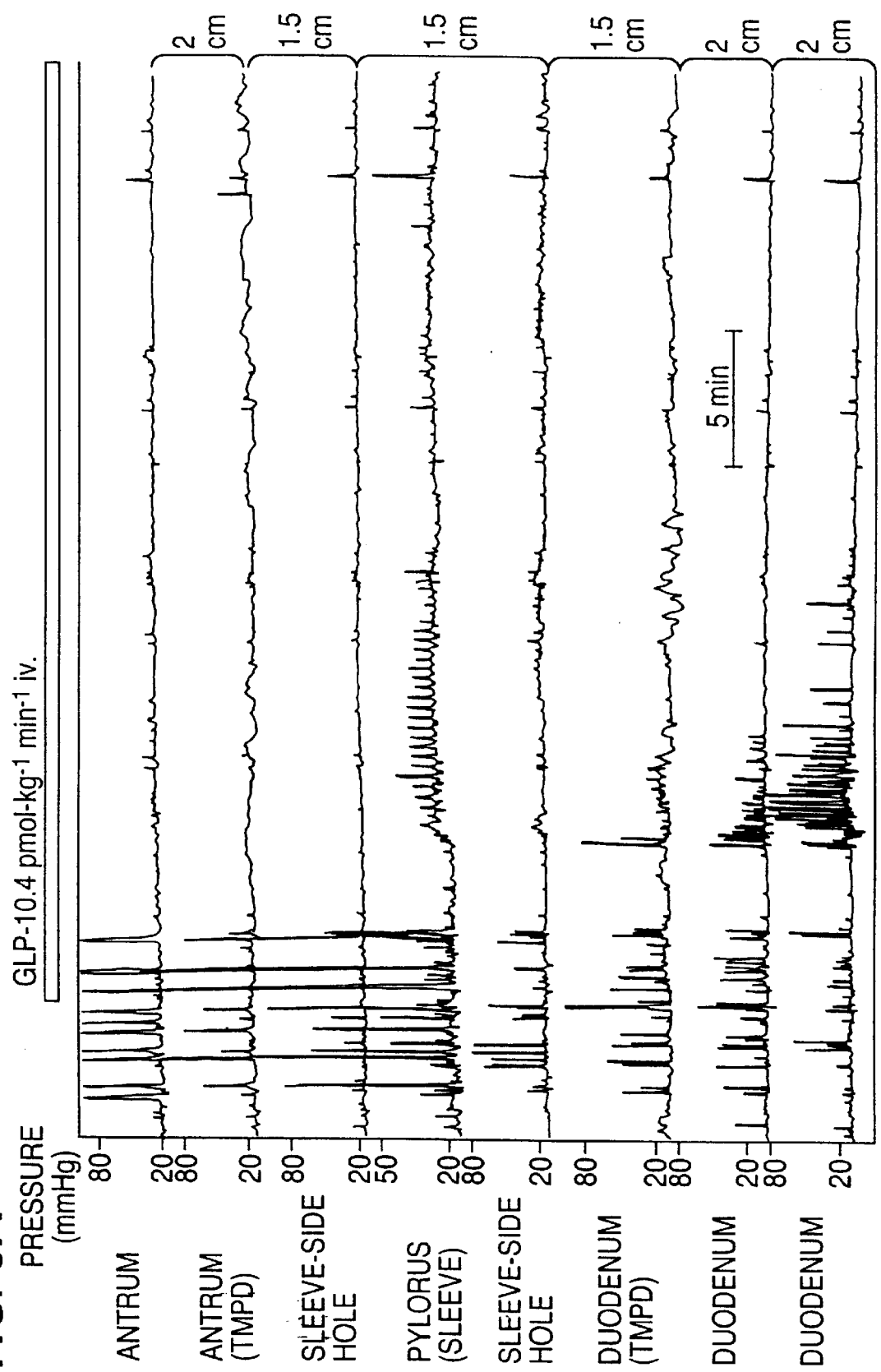

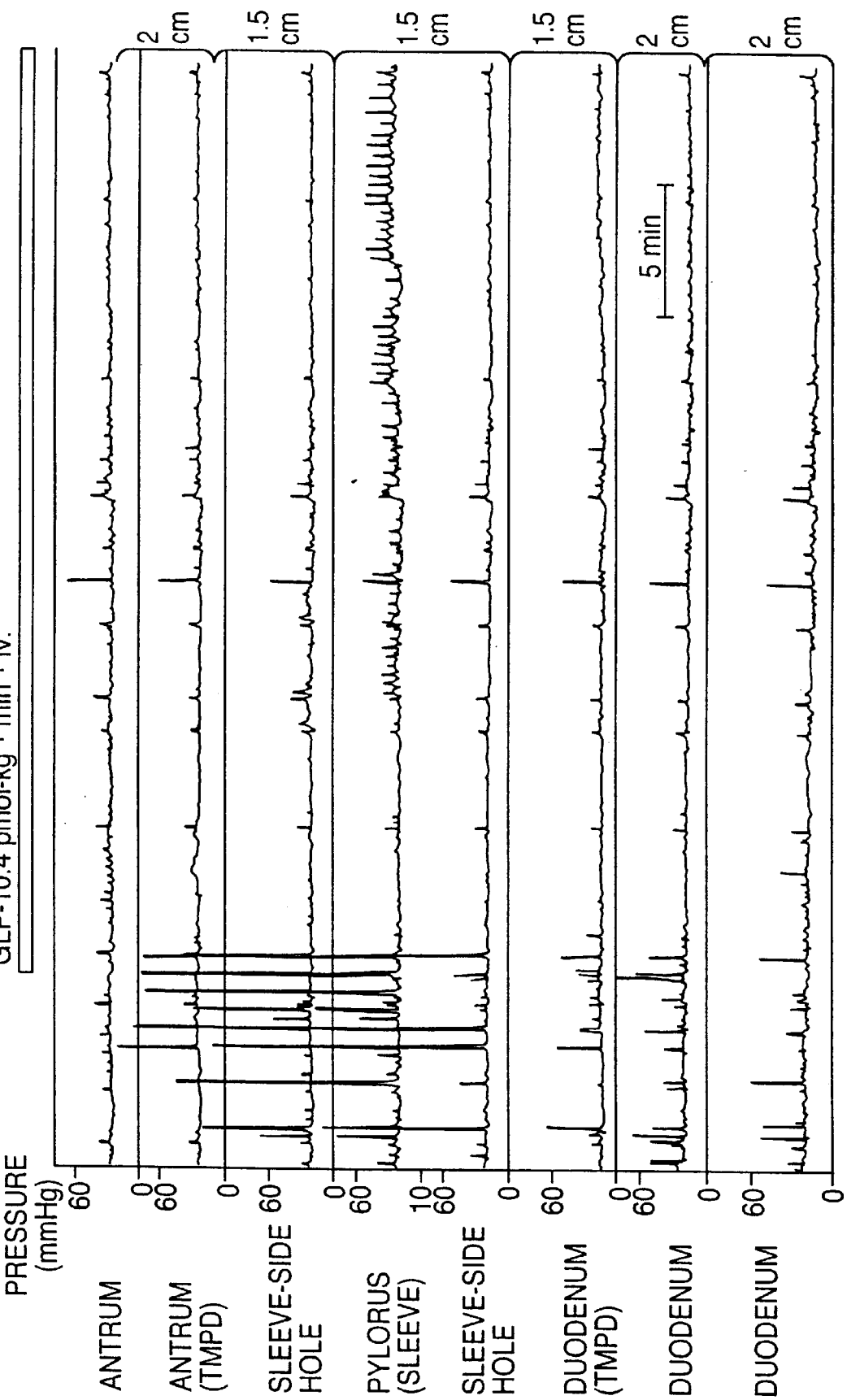

PLASMA GLUCOSE

INSULIN

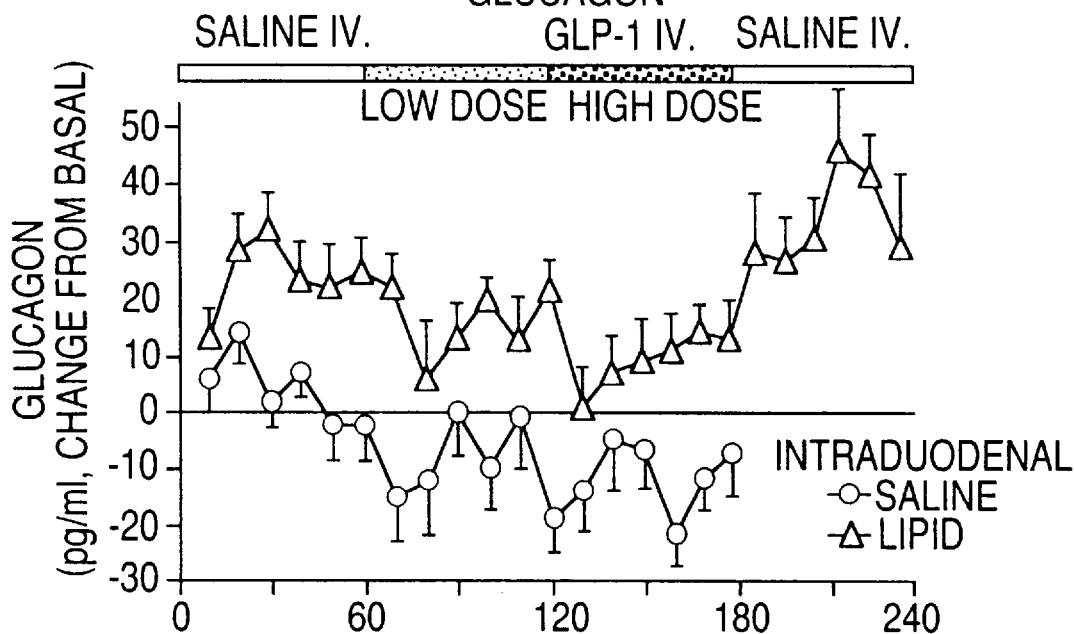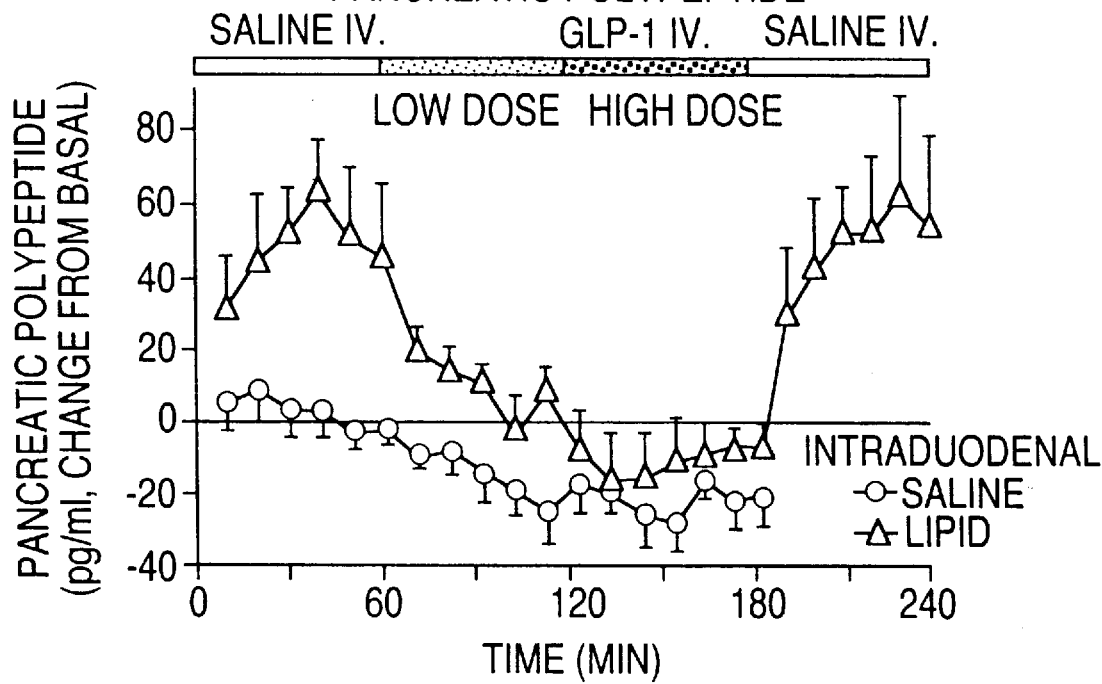

US 6,579,851 B2

EFFECTS OF GLUCAGON-LIKE PEPTIDE-1 (7-36) ON ANTRO-PYLORO-DUODENAL MOTILITY

This application claims priority to U.S. Provisional Application Serial No. 60/189,091, filed on Mar. 14, 2000, in the United States Patent and Trademark Office.

BACKGROUND OF THE INVENTION

1. Field of the Invention

The present invention relates to inhibiting antro-duodenal motility with GLP-1 and methods to alleviate discomfort during endoscopy and to alleviate symptoms of gastrointestinal disorders.

2. Description of the Related Art

Glucagon has been widely used to cause a variable reduction in gastroduodenal motility. The effect of glucagon appears to be dose-dependent with a minimally effective dose being 0.5 mg. Glucagon, however, does not facilitate colonoscopic evaluation (Norfleet, Gastrointest. Endosc., 24, 164–5, 1978), and at doses as high as 2 mg glucagon does not reduce contractions in the antrum (Gregerson et al., Scand. J. Gastroenterol. 23 (Supp 152), 42–47 (1988)). Furthermore, glucagon is contraindicated in persons with diabetes (Paul & Freyschmidt, ROFO Rortschr. Geb. Rontgenstr. Nuklearmed., 125, 31–7 (1996)), is expensive and its efficacy has been questioned.

Side effects associated with the use of glucagon include nausea and vomiting. The effects are dose-dependent and can appear at a dose of 1 mg (Larsen et al., Scand. J. Gastroenterol. 21, 634–640, 1986; Gregersen et al., supra, Diamant Handbook Experimental Pharm, Lefevre ed., Vol. 66/2, 611–643, 1983). As dosages required to sufficiently reduce motility frequently exceed 1 mg, side effects from glucagon use are common. Such side effects render the patient extremely uncomfortable and often cause the endoscopic procedure to be interrupted or aborted.

Hyoscamine sulfate has antispasmodic activity and been used for treatment of irritable bowel syndrome and also has adverse side effects (Lahoti et al., Gastrointest. Endosc. 46, 139–142 (1997)). Otreocide, a somatostatin analog, has also been used and proven effective in treating clinically significant diarrhea during rapid detoxification and postoperative dumping syndrome, but is associated with an unacceptable incidence of bradycardia; its long-term use is limited by side effects.

The proglucagon-derived glucagon-like peptide-1(7–36) amide (GLP-1) is a gastrointestinal hormone that is released postprandially from the L-cells of the gut (Göke et al., *Eur. J. Clin. Invest.* 21, 135–44 (1991); Schirra et al., *J. Clin. Invest.* 97, 92–103 (1996)). Previous studies in humans have shown synthetic GLP-1 to substantially retard gastric emptying of liquid and solid meals (Schirra et al., *J. Endocrinol,* 156, 177–86 (1998); Wettergren et al., *Dig. Dis. Sci.* 38, 665–673 (1993); Schirra et al., *Proc. Assoc. Am. Physicians* 109, 84–97 (1997)). Transpyloric pulsatile flow regulated by the motility of the antro-pyloro-duodenal region is a major mechanism of gastric emptying (Malbert & Mathis, *Gastroenterol.* 107, 37–46 (1994); Anvari et al., *J. Physiol.* (*London*) 488, 193–202 (1995)). Antral contractions, and especially antro-duodenal coordinated ones, were shown to be associated with the gastric emptying rate of liquids (Schirra et al., *J. Clin. Invest.* 97, 92–103 (1996); Camilleri et al., *Am J Physiol* 249, G580–585 (1985); Houghton et al., *Gastroenterol.* 94, 1276–84 (1988)) and solids (Fraser et al., *Am. J. Physiol.* 264, G195–201 (1993)). Tonic and localized phasic pressure increases generated by the pylorus provide an important braking mechanism, diminishing gastric outflow (Anvari et al., *J. Physiol.* (*London*) 488, 193–202 (1995); Heddle et al., *Dig. Dis. Sci.* 38, 856–69 (1993); Heddle et al., *Gut* 29, 1349–57 (1988); Tougas et al., *Gut* 33, 466–471 (1992)).

SUMMARY

It is therefore an object of the present invention to provide a method for inhibiting antro-duodenal motility with an effective, therapeutic composition that has minimal side effects. It is well known that GLP-1 does not cause hypoglycemia—and it did not cause hypoglycemia during the experiments discussed in the present application, nor did it cause any other side effects. Accordingly, a dosage unit comprising a GLP-1 molecule and a pharmaceutically suitable excipient is also disclosed.

In a related vein, the present invention also encompasses a method for premedicating in endoscopic procedures, comprising administering a GLP-1 molecule prior to or during an endoscopic procedure.

Another embodiment of the present invention is a method for treating or preventing gastrointestinal disorders, including but not limited to, irritable bowel syndrome, non-infectious acute and chronic diarrhea and post-operative dumping syndrome, that comprises administering to the patient therapeutically effective amount of a GLP-1 molecule.

Further encompassed by this invention is a method for treating or preventing symptoms associated with narcotics withdrawal, by administering a GLP-1 molecule as described above.

In another embodiment, the invention includes a method for inhibiting pyloric motility in a patient in need thereof that comprises administering to the patient a therapeutically effective amount of an antagonist to a GLP-1 molecule.

DESCRIPTION OF FIGURES

FIG. 1. Plasma immunoreactivities of GLP-1 in response to intravenous infusions of saline, GLP-1(7–36)amide at 0.4 and 1.2 pmol·kg$^{-1}$·min$^{-1}$ with concomitant duodenal perfusion of saline or lipid (2.5 kcal/min) in eleven healthy volunteers. Mean±SEM. For statistical analysis, see Table 3.

FIG. 4. Occurrence of duodenal phase III-like activity with duodenal perfusion of saline (upper panel) or lipid (2.5 kcal/min, lower panel) in eleven healthy volunteers. In seven of eleven subjects an activity front was seen within 10 min, after start of low dose GLP-1 in the interdigestive state or duodenal lipid perfusion in the postprandial studies, respectively. Length of solid bars represents length of contraction burst.

FIG. 5. Manometric tracings showing the effects of intravenous infusion of GLP-1 at 0.4 pmol·kg$^{-1}$·min$^{-1}$ during duodenal perfusion of saline (A) and lipid (2.5 kcal/min, B). In the interdigestive state (A), GLP-1 immediately inhibits antroduodenal motility, and induces a sustained increase of basal pyloric pressure with a concomitant short lasting stimulation of IPPWs. During duodenal lipid perfusion (B), antral and duodenal contractility are abolished with GLP-1, and basal pyloric pressure further increases in addition to the effect of lipid alone paralleled by a stimulation of IPPWs.

DETAILED DESCRIPTION

Figure 2B:
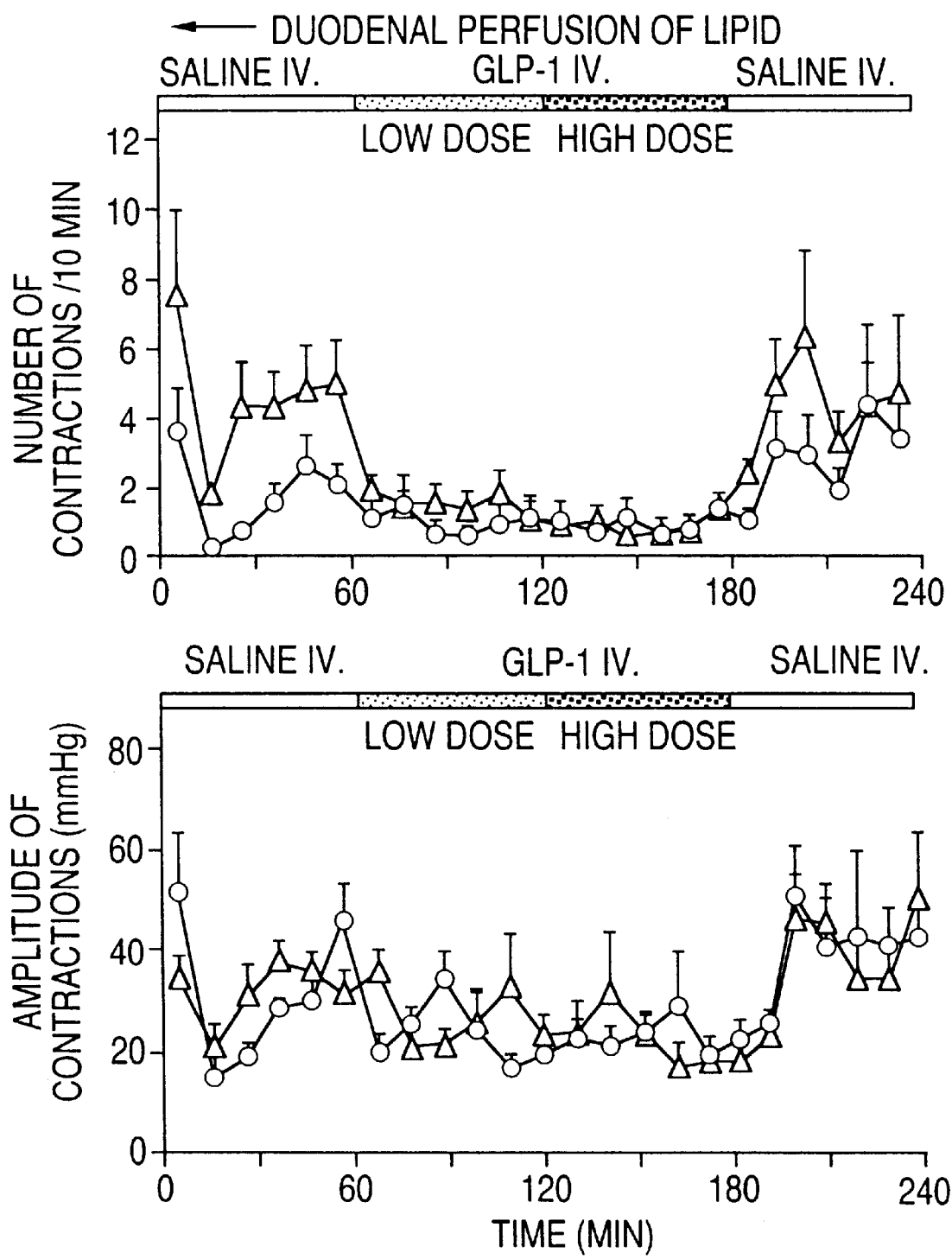
FIG. 2. Contraction frequencies (upper panel) and amplitudes (lower panel) in the antrum and duodenum in response to intravenous infusions of saline, GLP-1(7–36)amide at 0.4 and 1.2 pmol·kg$^{-1}$·min$^{-1}$ during concomitant duodenal perfusion of saline (A) or lipid (2.5 kcal/min, B) in eleven healthy volunteers. Mean±SEM. For statistical analysis, see Table 1.

Previous studies in humans have shown synthetic GLP-1 to substantially retard gastric emptying of liquid and solid meals (Schirra et al., *J. Endocrinol,* 156, 177–86 (1998); Wettergren et al., *Dig. Dis. Sci.* 38, 665–673 (1993); Schirra et al., *Proc Assoc Am Physicians* 109, 84–97 (1997)). In addition to its insulinotropic and glucagonostatic action, reduction of the gastric emptying rate may be considerably involved in the glucose-lowering effect of GLP-1 in healthy subjects and patients with diabetes mellitus (Schirra et al., *J. Endocrinol,* 156, 177–86 (1998); Schirra et al., *Proc Assoc Am Physicians* 109, 84–97 (1997)). Independent of the tonic pressure generated by the proximal stomach, transpyloric pulsatile flow regulated by the motility of the antro-pyloro-duodenal region is a major mechanism of gastric emptying (Malbert & Mathis, *Gastroenterol.* 107, 37–46 (1994); Anvari et al., *J. Physiol.* (*London*) 488, 193–202 (1995)). Antral contractions, and especially antro-duodenal coordinated ones, were shown to be associated with the gastric emptying rate of liquids (Schirra et al., *J. Clin. Invest.* 97, 92–103 (1996); Camilleri et al., *Am J Physiol* 249, G580–585 (1985); Houghton et al., *Gastroenterol.* 94, 1276–84 (1988)) and solids (Fraser et al., *Am. J. Physiol.* 264, G195–201 (1993)). Tonic and localized phasic pressure increases generated by the pylorus provide an important braking mechanism diminishing gastric outflow (Anvari et al., *J. Physiol.* (*London*) 488, 193–202 (1995); Heddle et al., *Dig. Dis. Sci.* 38, 856–69 (1993); Heddle et al., *Gut* 29, 1349–57 (1988); Tougas et al., *Gut* 33, 466–471 (1992)).

The present application describes the effects of graded doses of synthetic GLP-1 on the motility of the antro-pyloro-duodenal region during the interdigestive and postprandial state in human, the latter being elicited by duodenal perfusion of lipid. Duodenal perfusion of lipid was used, instead of oral meal ingestion, to provide a constant duodenal nutrient load independent of gastric emptying. This particular meal was chosen to establish a stable postprandial motility pattern, and in order to minimize plasma glucose and insulin excursions. Finally, the effects of GLP-1 were compared with those of lipid, the classical physiological stimulator of pyloric motility.

The applicants have discovered that GLP-1 provides a cost-effective therapeutic composition for use in preventing or treating various gastrointestinal disorders. Furthermore, GLP-1 can be used to premedicate for endoscopy and treat symptoms of narcotics withdrawal. Other medications do not share the same effectiveness as GLP-1 and are often accompanied by adverse side effects. Such side effects include, but are not limited to, nausea and vomiting. These side effects have not been observed in LP-1 treated patients.

Assessing Gastric Motility

Inhibition of antro-duodenal activity is assessed directly by motility recordings using methods that are well known to the skilled artisan. Contractile events are analyzed with a computer and validated software (Katschinski et al., *Gastroenterol.* 103, 383–91 (1992)) and only peaks with amplitudes of at least 10 mmHg and a duration of at least 2 s are considered true contractions. Duodenal phase III is defined as the occurrence of regular contractions at a frequency of ≧10/min for at least 2 min in the duodenum propagated aborally.

In one embodiment, the data are analyzed in 10-min segments separately for antrum and duodenum by summarizing (frequency, motility index) or averaging (amplitude) the values derived from, the two antral and three duodenal side holes, respectively. Motility indexes are identified as the area under the contractions and are expressed in mmHg·s·min$^{-1}$. Antral contractions are determined to be antro-pyloro-duodenally propagated waves if the onset of the pressure wave recorded in the most proximal duodenal side hole, occurs within 5 sec after the onset of a pressure wave recorded in one of the antral side holes and if both wave are registered by all side holes in between.

As used herein, "inhibition" of antro-pyloro-duodenal motility is defined as a reduction in the motility index. Other methods for measuring motility can be used. One of skill in the art will appreciate that a significant inhibition, including total inhibition, of motility will be useful. Pyloric tone can be calculated as change from basal, the latter being determined as mean pyloric tone during the basal period before starting the experiments.

GLP-1 Molecules

As used herein, a "GLP-1 molecule" includes the following. Mammalian GLP peptides and glucagon are encoded by the same gene. In the ileum the phenotype is processed into two major classes of GLP peptide hormones, namely GLP-1 and GLP-2. GLP-1(1–37) has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:1). GLP-1 (1–37) is amidated post-translationally to yield GLP-1(1–36)NH$_2$, which has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) (SEQ ID NO:2); or is enzymatically processed to yield GLP-1(7–37), which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:3). GLP-1(7–37) can also be amidated to yield GLP-1(7–36)amide, which is the natural form of the GLP-1 molecule, and which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) (SEQ ID NO:4). Likewise, GLP-1(1–36) (NH$_2$) can be processed to GLP-1(7–36)(NH$_2$).

Intestinal L cells secrete GLP-1(7–37) (SEQ ID NO:3) and GLP-1(7–36)NH$_2$ (SEQ ID NO:4) in a ratio of 1 to 5, respectively. These truncated forms of GLP-1 have short half-lives in situ, i.e., less than 10 minutes, and are inactivated by an aminodipeptidase IV to yield Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5); and Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) (SEQ ID NO:6); respectively. The peptides Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5) and Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) (SEQ ID NO:6), have been speculated to affect hepatic glucose production, but do not stimulate production or release of insulin from the pancreas.

As used in this specification, the term "GLP-1 molecule" includes GLP-1(1–37), GLP-1(1–36)NH$_2$, GLP-1(7–37), GLP-1(7–36)NH$_2$ ("GLP-1(7–36) amide ") (collectively referred to as "GLP-1 peptides"). The present invention includes the use of recombinant human GLP-1 peptides as well as GLP-1 peptides derived from other species, whether recombinant or synthetic.

"GLP-1 molecule" further denotes biologically active variants, analogs, and derivatives of GLP-1 peptides. "Biologically active," in this context, means having GLP-1 (7–36) biological activity, but it is understood that the activity of the variant can be either less potent or more potent than native GLP-1(7–36)amide. GLP-1(7–36)amide is a native, biologically active form of GLP-1. See Göke & Byrne, *Diabetic Medicine,* 13, 854–860 (1996). GLP-1 molecules of the present invention include polynucleotides that express agonists of GLP-1, i.e. activators of the GLP-1 receptor molecule and its secondary messenger activity found on, inter alia, insulin-producing β-cells. GLP-1 mimetics that also are agonists of β-cells include, for example, chemical compounds specifically designed to activate the GLP-1 receptor.

GLP-1 molecule biological activity can be determined by in vitro and in vivo animal models and human studies as is well known to the skilled artisan. Included as GLP-1 molecules are any molecules, whether they be peptides, peptide mimetics, or other molecules that bind to or activate a GLP-1 receptor, such as the GLP-1(7–36)amide receptor, and its second messenger cascade. GLP-1 receptors are cell-surface proteins found, for example, on insulin-producing pancreatic β-cells. The GLP-1(7–36) receptor has been characterised in the art. Methods of determining whether a chemical or peptide binds to or activates a GLP-1 receptor are known to the skilled artisan and are preferably carried out with the aid of combinatorial chemical libraries and high throughput screening techniques. GLP-1 molecules include species having insulinotropic activity and that are agonists of, i.e. activate, the GLP-1 receptor molecule and its second messenger activity on, inter alia, insulin-producing β-cells.

GLP-1 biological activity can be determined by standard methods, in general, by receptor-binding activity screening procedures which involve providing appropriate cells that express the GLP-1 receptor on their surface, for example, insulinoma cell lines such as RINmSF cells or INS-1 cells. See also Mojsov, Int J Pept Protein Res 40, 333–43 (1992) and EPO708170A2. Cells that are engineered to express a GLP-1 receptor also can be used. In addition to measuring specific binding of tracer to membrane using radioimmunoassay methods, cAMP activity or glucose dependent insulin production can also be measured. In one method, a polynucleotide encoding the receptor of the present invention is employed to transfect cells to thereby express the GLP-1 receptor protein. Thus, for example, these methods may be employed for screening for a receptor agonist by contacting such cells with compounds to be screened and determining whether such compounds generate a signal, i.e. activate the receptor.

Polyclonal and monoclonal antibodies can be utilized to detect purify and identify GLP-1 like peptides for use in the methods described herein. Antibodies such as ABGA1178 detect intact unprocessed GLP-1(1–37) or N-terminally-truncated GLP-1(7–37) or (7–36)amide. Other antibodies detect on the very end of the C-terminus of the precursor molecule, a procedure which allows by subtraction to calculate the amount of biologically active truncated peptide, i.e. GLP-1(7–37)amide (Orskov et al., Diabetes, 42, 658–661 (1993); Orskov et al., *J. Clin. Invest.* 87, 415–423 (1991)).

Other screening techniques include the use of cells which express the GLP-1 receptor, for example, transfected CHO cells, in a system which measures extracellular pH or ionic changes caused by receptor activation. For example, potential agonists may be contacted with a cell which expresses the GLP-1 protein receptor and a second messenger response, e.g. signal transduction or ionic or pH changes, may be measured to determine whether the potential agonist is effective.

Agonists of glucagon-like peptide that exhibit activity through the GLP-1(7–36)amide receptor have been described. See EP 0708179A2; Hjorth et al., *J. Biol. Chem.* 269; 30121 (1994); Siegel et al., Amer. Diabetes Assoc. 57th Scientific Session, Boston (1997); Hareter et al, Amer. Diabetes Assoc. 57th Scientific Session, Boston (1997); Adelhorst et al., *J. Biol. Chem.* 269, 6275 (1994); Deacon et al, 16th International Diabetes Federation Congress Abstracts, *Diabetologia Supplement* (1997); Irwin et al., *Proc. Natl. Acad. Sci. USA* 94; 7915 (1997); Mojsov, *Int. J. Peptide Protein Res.* 40; 333 (1992). Göke & Byrne, *Diabetic Medicine* 13; 854 (1996). Recent publications disclose Black Widow GLP-1 and Ser$^2$ GLP-1. See Holz & Hakner, *Comp. Biochem. Physiol.*, Part B 121; 177 (1998) and Ritzel et al., *J. Endocrinol* 159; 93 (1998).

"GLP-1 molecules" also include peptides that are encoded by polynucleotides that express biologically active GLP-1 variants as defined herein. Also included in the present invention are GLP-1 molecules that are peptides containing one or more amino acid substitutions, additions or deletions, compared with GLP-1(7–36) amide. In one embodiment, the number of substitutions, deletions, or additions is 30 amino acids or less, 25 amino acids or less, 20 amino acids or less, 15 amino acids or less, 10 amino acids or less, 5 amino acids or less or any integer in between these amounts. In one aspect of the invention, the substitutions include one or more conservative substitutions. A "conservative" substitution denotes the replacement of an amino acid residue by another, biologically active similar residue. Examples of conservative substitution include the substitution of one hydrophobic residue, such as isoleucine, valine, leucine or methionine for another, or the substitution of one polar residue for another, such as the substitution of arginine for lysine, glutamic for aspartic acids, or glutamine for asparagine, and the like. The following table lists illustrative, but non-limiting, conservative amino acid substitutions.

| ORIGINAL RESIDUE | EXEMPLARY SUBSTITUTIONS |
|---|---|
| ALA | SER, THR |
| ARG | LYS |
| ASN | HIS, SER |
| ASP | GLU, ASN |
| CYS | SER |
| GLN | ASN, HIS |

-continued

| ORIGINAL RESIDUE | EXEMPLARY SUBSTITUTIONS |
|---|---|
| GLU | ASP, GLU |
| GLY | ALA, SER |
| HIS | ASN, GLN |
| ILE | LEU, VAL, THR |
| LEU | ILE, VAL |
| LYS | ARG, GLN, GLU, THR |
| MET | LEU, ILE, VAL |
| PHE | LEU, TYR |
| SER | THR, ALA, ASN |
| THR | SER, ALA |
| TRP | ARG, SER |
| TYR | PHE |
| VAL | ILE, LEU, ALA |
| PRO | ALA |

It is further understood that GLP-1 peptide variants include the above described peptides, which have been chemically derivatized or altered, for example, peptides with non-natural amino acid residues (e.g., taurine residue, β- and γ-amino acid residues and D-amino acid residues), C-terminal functional group modifications, such as amides, esters, and C-terminal ketone modifications and N-terminal functional group modifications, such as acylated amines, Schiff bases, or cyclization, such as found, for example, in the amino acid pyroglutamic acid.

Also included in the present invention are peptide sequences having greater than 50 percent sequence identity, and preferably greater than 90 percent sequence identity to (1) SEQ ID NOS:1, 2, 3, 4; and (2) to truncated sequences thereof. As used herein, sequence identity refers to a comparison made between two molecules using standard algorithms well known in the art. The preferred algorithm for calculating sequence identity for the present invention is the Smith-Waterman algorithm, where SEQ ID NO:1 is used as the reference sequence to define the percentage identity of polynucleotide homologs over its length. The choice of parameter values for matches, mismatches, and inserts or deletions is arbitrary, although some parameter values have been found to yield more biologically realistic results than others. One preferred set of parameter values for the Smith-Waterman algorithm is set forth in the "maximum similarity segments" approach, which uses values of 1 for a matched residue and −⅓ for a mismatched residue (a residue being either a single nucleotide or single amino acid) (Waterman, Bull.Math. Biol. 46, 473–500 (1984)). Insertions and deletions (indels), x, are weighted as $$X_k = 1 + k/3,$$

where k is the number of residues in a given insert or deletion (Id.).

For instance, a sequence that is identical to the 42 amino acid residue sequence of SEQ ID NO:1, except for 18 amino acid substitutions and an insertion of 3 amino acids, would have a percent identity given by:

[(1×42 matches)−(⅓×18 mismatches)−(1+⅔ indels)]/42=81% identity

Also included in "GLP-1 molecules" of the present invention are six peptides in Gila monster venoms that are homologous to GLP-1. Their sequences are compared to the sequence of GLP-1 in Table 1.

TABLE I

Position 1

| | |
|---|---|
| a. | H A E G T F T S D V S S Y L E G Q A A K E F I A W L V K G R (NH₂) |
| b. | H S D G T F T S D L S K Q M E E E A V R L F I E W L K N G G P S S S G A P P P S (NH₂) |
| c. |                 D L S K Q M E E E A V R L F I E W L K N G G P S S G A P P P S (NH₂) |
| d. | H G E G T F T S D L S K Q M E E E A V R L F I E W L K N G G P S S G A P P P S (NH₂) |
| e. | H S D A T F T A E Y S K L L A K L A L Q K Y L E S I L G S S T S P R P P S S |
| f. | H S D A T F T A E Y S K L L A K L A L Q K Y L E S I L G S S T S P R P P S |
| g. | H S D A I F T E E Y S K L L A K L A L Q K Y L A S I L G S R T S P P P (NH₂) |
| h. | H S D A I F T Q Q Y S K L L A K L A L Q K Y L A S I L G S R T S P P P (NH₂) | a = GLP-1(7–36)amide (SEQ. ID NO: 4)
b = exendin 3 (SEQ. ID NO: 7).
c = exendin 4 (9–39(NH₂) (SEQ. ID NO: 8).
d = exendin 4 (SEQ. ID NO: 9).
e = helospectin I (SEQ. ID NO: 10).
f = helospectin II (SEQ. ID NO: 11).
g = helodermin (SEQ. ID NO: 12).
h = $Q^8$, $Q^9$ helodermin (SEQ. ID No:13).

Peptides (a, b, d, e, f and g) are homologous in positions 1, 7, 11 and 18. GLP-1 and exendins are further homologous in positions, 4, 5, 6, 8, 9, 15, 22, 23, 25, 26 and 29. In position 2, A, S and G are structurally similar. In position 3, residues D arid E (Asp and Glu) are structurally similar. In positions 22 and 23, F (Phe) and I (Ile) are structurally similar to Y (Tyr) and L (Leu), respectively. Likewise, in position 26, L and I are structurally equivalent. Thus, of the 30 residues of GLP-1, exendins 3 and 4 are identical in 15 positions and equivalent in 5 additional positions. The only positions where radical structural changes are evident are at residues 16, 17, 19, 21, 24, 27, 28 and 30. Exendins also have 9 extra residues at the carboxyl terminus.

The GLP-1 molecules of the invention that are peptides that can be made by solid state chemical peptide synthesis. Such peptides can also be made by conventional recombinant techniques using standard procedures described in, for example, Sambrook & Maniatis. "Recombinant", as used herein, means that a gene is derived from a recombinant (e.g., microbial or mammalian) expression system which has been genetically modified to contain polynucleotide encoding a GLP-1 molecule as described herein.

The GLP-1 like peptides can be recovered and purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography (HPLC) can be employed for final purification steps.

The GLP-1 molecule peptides of the present invention may be a naturally purified product, or a product of chemical synthetic procedures, or produced by recombinant techniques from prokaryotic or eukaryotic hosts (for example by bacteria, yeast, higher plant, insect and mammalian cells in culture or in vivo). Depending on the host employed in a recombinant production procedure, the polypeptides of the present invention are generally non-glycosylated, but may be glycosylated.

Particularly preferred GLP-1 molecules of the invention are GLP-1(7–36)amide, and GLP-1(7–37) and exendin-4.

Synthetic GLP-1(7–36)amide can be purchased and delivered with a peptide content of 87.1% and a peptide purity of >99%. According to known methods in the field, the peptide can be dissolved in 1% human serum albumin, filtered through 0.2 μm nitrocellulose filters and then stored at −70° C. [13]. Samples are tested for pyrogens and bacterial growth standard techniques.

Without being bound by a particular mechanism, the present inventor suggests that the following motor effects of GLP-1 are important mediators of reduced antro-duodenal motility: (i) inhibition of antral waves in general, (ii) reduction of transpyloric propagated antral waves in particular and (iii) simultaneous stimulation of localized phasic and tonic pyloric contractions. In dogs, a similar motor pattern has been demonstrated to be associated with reduction of transpyloric flow and inhibition of gastric emptying of a non-caloric liquid meal with infusion of synthetic GLP-1 (Anvari et al., *Dig. Dis. Sci.* 43, 1133–40 (1998)). In human, subcutaneously injected GLP-1 dose-dependently inhibits antral and coordinated antroduodenal contractions parallel to prolongation of the gastric emptying lag phase of a mixed liquid meal (Schirra et al. *Proc. Assoc. Am. Physicians* 109, 84–97 (1997)). Additionally, preliminary data obtained from human studies indicate a strong relaxation of the proximal stomach in response to intravenous GLP-1 using the same dosages as in the present study (Wank et al., *Gastroenterol.* 114, A1190 (abstract) (1998)). Thus, exogenous GLP-1 reduces driving forces and stimulates braking mechanisms of gastric outflow, thereby impacting on all motor sites known to determine gastric emptying.

Formulating a Dosage Unit

Another embodiment of the present invention is a dosage unit for use in inhibiting antro-duodenal motility in a patient comprising GLP-1 and a pharmaceutically suitable excipient is described. Preferably, the dosage unit is in the range of about 0.4 to 2.4 pmol·kg$^{-1}$·min$^{-1}$. Still more preferably, the dosage unit is in the range of about 0.8 to 1.2 pmol·kg$^{-1}$·min$^{-1}$. For the purpose of this invention, the term "about" is defined as +/−10%. For example, a dosage unit in the range of about 0.4 to 2.4 pmol·kg$^{-1}$·min$^{-1}$ means 0.196 to 2.64 pmol·kg$^{-1}$·min$^{-1}$.

The composition of the present invention can be used as a systematic or local application by oral or parenteral administration. Alternatively, the composition may be applied as an intravenous or subcutaneous injection. For use by the physician or patient, the composition may be provided in a dosage unit form containing an amount of a GLP-1 molecule, for example, a GLP-1(7–36)amide, with or without another antimotility agent. This will be effective in one or multiple doses for use in the inihibition of antro-duodenal motility. As will be recognized by those in the field, an effective amount of therapeutic agent will vary with many factors including the age and weight of the patient, the patient's physical condition and other factors. Preferably, a GLP-1 molecule is administered intravenously and the dosage unit is in the range of about 0.4 to 2.4 pmol·kg$^{-1}$·min$^{-1}$. Still more preferably, the dosage unit is in the range of about 0.8 to 1.2 pmol·kg$^{-1}$·min$^{-1}$.

The solid composition for oral administration of the present invention includes tablets, preparations, granules and the like. In such a solid composition, one or more active ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the usual work-up, the composition may contain additives other than inactive diluent, for example, lubricant such as magnesium stearate; disintegrant such as fibrous calcium gluconate; stabilizer such as cyclodextrin, for example, α,β- or γ-cyclodextrin; etherified cyclodextrin such as dimethyl-α-, dimethyl-β-, trimethyl-β-, or hydroxypropyl-β-cyclodextrin; branched cyclodextrin such as glucosyl-, maltosyl-cyclodextrin; formylated cyclodextrin, cyclodextrin containing sulfur; phospholipid and the like. When the above cyclodextrins are used, inclusion compound with cyclodextrins may be sometimes formed to enhance stability. Alternatively, phospholipid may be sometimes used to form liposome, resulting in enhanced stability.

Tablets or pills may be coated with film soluble in the stomach or intestine such as sugar, gelatin, hyroxypropyl cellulose, hydroxypropylmethyl cellulose phthalate as needed. Further, they may be formed as capsules with absorbable substances such as gelatin.

A liquid composition for oral administration may contain pharmaceutically acceptable emulsion, solution, suspension, syrup, elixer as well as generally used inactive diluent. Such composition may contain, in addition to the inactive diluent, adjuvants such as lubricants and suspensions, sweetening agents, flavoring agents, preservatives, solubilizers, anti-oxidants and the like. The details of the additives may be selected from those described in any general textbook in the pharmaceutical field. Such liquid compositions may be directly enclosed in soft capsules.

Solutions for parenteral administration, for example, suppository, enema and the like according to the present invention include sterile, aqueous or non-aqueous solution, suspension, emulsion, detergent and the like. The aqueous solution and suspension includes, for example, distilled water, physiological saline and Ringer's solution.

The non-aqueous solution and suspension include, for example, propylene glycol, polyethylene glycol, fatty acid triglyceride, vegetable oil such as olive oil, alcohols such as ethanol, polysorbate and the like. Such composition may contain adjuvants such as preservatives, wetting agent, emulsifier, dispersant, anti-oxidants and the like.

Inhibiting Antro-duodenal Motility

The present invention encompasses a method for inhibiting antro-duodenal motility in a patient in need thereof, which comprises administering to the patient a composition comprising a GLP-1 molecule in a therapeutically effective amount. In a preferred embodiment, said GLP-1 molecule is GLP-1(7–36)amide. As described throughout the specification, the GLP-1 molecule can be administered using a variety of methods. Furthermore, as described herein, there are a variety of patients that will benefit from the inhibition of antro-duodenal motility, using the inventive methods. The term "patient" as used herein refers to any mammal, including a human.

Premedicating with GLP-1

Included in this invention is a method for premedicating in endoscopic procedures, which comprises administering to the patient a composition comprising a GLP-1 molecule in a therapeutically effective amount. Premedication is intended to reduce a patient's discomfort in endoscopic procedures and the like, by reducing antro-duodenal motility. Contraction or spasm of gastrointestinal smooth muscle imposes a technical obstacle, which must frequently be overcome in order to enable the clinician to successfully, perform endoscopic procedures. "Premedication" includes administration of a GLP-1 molecule just prior to, or during the procedure. "Just prior to" means up to about 1 hour before beginning the procedure or before scope insertion, and "during" means any time during the procedure, including at cecal intubation and before or during scope withdrawal. Just prior to includes administration of a GLP-1 molecule up to about 45, 30, 20, 15, 10, 5 minutes, or 1 minute before beginning the procedure or before scope insertion. The term "endoscope" or "scope" is used to refer to a colonoscope, gastroscope, enteroscope, cytoscope or other types of medical endoscopes.

The term "endoscopic procedures" refers to those diagnostic procedures that utilize an instrument that is introduced into the gastrointestinal tract to provide direct visualization of the gastrointestinal tract, for examination and therapeutic purposes. Such purposes include direct visualization, biopsy, access to the common bile duct, fluid aspiration and removal of foreign bodies, polyps, and other lesions. An example of a particular endoscopic procedure is esophagogastro-duodenoscopy, which is utilized for examination of the esophageal lumen, stomach and duodenum. Another example, endoscopicretrograde cholangiopanereatography (ERCP), enables visualization of the pancreatic duct, common bile duct and the entire biliary tract, including the gall bladder. Further examples of endoscopic procedures are colonoscopy, signoidoscopy and barium enema examinations.

Treating and Preventing Gastrointestinal Disorders

Another facet of this invention is a method for treating or preventing non-infectious acute and chronic diarrhea in a patient in need thereof which comprises administering to the patient a composition comprising a GLP-1 molecule in a therapeutically effective amount. "Acute" is defined as a short and relatively severe course and "chronic" means persisting over longer periods of time (Dorland's Medical Dictionary, 27$^{th}$ Edition). "Non-infectious" implies not caused by, or capable of being communicated by infection, as an infectious disease (Dorland's Medical Dictionary, 27$^{th}$ Edition).

In a related vein, the invention includes a method for treating or preventing postoperative "dumping syndrome" in a patient in need thereof, which comprises administering to the mammal a GLP-1 molecule in a therapeutically effective amount. Dumping syndrome is one of the most common causes of morbidity after gastric surgery and can occur in patients after damage to the vagal nerve in esophageal surgery (Vecht et al). It is characterized by both gastrointestinal and vasomotor symptoms. Gastrointestinal symptoms include postprandial fullness, crampy abdominal pain, nausea, vomiting and explosive diarrhea. Vasomotor symptoms include diaphoresis, weakness, dizziness, flushing, palpitations, and an intense desire to lie down. Patients with severe dumping symptoms may limit their food intake to minimize symptoms and as a result lose weight and become malnourished. In severe cases, as a last resort surgical treatment of dumping syndrome has been utilized.

Pharmaceutical treatment for severe dumping includes octreotide acetate (Sandoz), a long acting somatostatin analog, which has been used with some success. Octreotide is administered subcutaneously and acts to slow gastric emptying, inhibit insulin release, and decrease enteric peptide secretion. Octreotide, however, is accompanied by several complications, including injection site pain, tachyphylaxis, iatrogenic diabetes, malabsorption and cholelithiasis.

In another embodiment, the invention includes a method for treating or preventing irritable bowel syndrome (IBS) in a patient in need thereof, which comprises administering to the patient a GLP-1 molecule in a therapeutically effective amount.

IBS is believed to be a heterogeneous group of disorders, characterized by chronic lower gastrointestinal symptoms not associated with an identifiable organic cause. The "spastic" variety of IBS, which is characterized by abdominal pain and constipation, is believed to be more common than IBS associated with chronic diarrhea and postprandial urgency. However, as noted above, the "diarrhea predominance" variety is also common.

The definition and diagnosis of IBS have been somewhat controversial, but attempts have been made in recent years to reach some consensus regarding the definition of IBS and other functional or non-organic GI disorders, and the clinical criteria for their diagnosis (Drossman et al., supra; Hasler et al., supra; Camilleri et al., supra; Drossman et al., supra; Thompson et al., 1989, Gastroenterol. Intl. 2:92–95; Manning et al., 1978, Br. Med. J. 2:653–654 and Thompson et al., supra). According to the so-called "Rome criteria," patients afflicted with chronic diarrhea not attributable to an organic cause and not accompanied by significant abdominal pain are classified as having functional diarrhea, and those patients afflicted with chronic diarrhea not attributable to an organic cause and accompanied by significant abdominal discomfort are classified as having IBS with diarrhea predominance (Drossman et al., supra; Hasler et al.,supra; Camilleri et al., supra; Drossman et al., supra; Thompson et al., supra; Manning et al., supra).

In another aspect, the invention is directed to a method for treating or preventing symptoms associated with narcotics withdrawal in a patient in need thereof, which comprises administering to the patient a GLP-1 molecule in a therapeutically effective amount. Clinically significant diarrhea is commonly seen during the acute phase of withdrawal in persons addicted to narcotics such as heroin and methadone. Loose stool and diarrhea frequently accompany the acute reaction of withdrawal from opioid drugs. The problem becomes even more severe when patients are sedated during the procedure, as they lose bowel control.

Assessing Pyloric Motility

The present invention also relates to therapeutic methods associated with stimulating pyloric motility. Two parameters used to describe pyloric motility are: 1) Isolated pyloric pressure waves (IPPW), defined as contractions registered by the sleeve with or without simultaneous contractions in maximally one sleeve-side-hole in the absence of associated (±3 sec) waves of any amplitude in the adjacent antral and duodenal side-holes and 2) pyloric tone. Pyloric tone is measured by deducting the basal pressure recorded by the antral side hole at the proximal end of the sleeve, from the basal pressure recorded by the sleeve. Basal pressures is defined as the mean pressure after excluding contractions; it is obtained each minute and used to calculate mean pyloric tone.

The invention also includes a method for inhibiting pyloric motility in a patient in need thereof, which comprises administering to the patient a GLP-1 antagonist in a therapeutically effective amount. Also described in the examples, GLP-1 stimulated pyloric motility. The effects of GLP-1 in relation to those of lipid, the classical physiological stimulator of pyloric motility, were compared.

A comparison of pyloric stimulation by GLP-1, with and without duodenal lipid, provides new insights in the regulation of pyloric motility. Pyloric tone stably increases with both duodenal lipid and exogenous GLP-1 and the tonic response to duodenal lipid can be further enhanced by exogenous GLP-1. GLP-1 can stimulate pyloric tone at least as strong as duodenal lipid, and the interaction of both was additive. Conversely, GLP-1 was not able to stimulate IPPWs as strong as duodenal lipid, even at supraphysiological levels. Thus, the phasic pyloric response to duodenal lipid may be less dependant on GLP-1 release, and the mechanisms for GLP-1 stimulation of pyloric motility may be different than that of lipid.

EXAMPLES

The following examples illustrate the present invention but are not in any way intended to limit the scope of this invention. The following abbreviations are used in the examples below.

| IPPW | isolated pyloric pressure wave |
| --- | --- |
| PP | pancreatic polypeptide |
| CCK | cholecystokinin |

Measurement of Plasma Hormone Levels and GLP-1

Plasma glucose concentrations were measured using a glucose analyzer by the glucose oxidase method (YSI 1500 G; Schlag, Bergisch-Gladbach, Germany), with a coefficient of variation of <2%. Plasma insulin was measured by the Abbott Imx Microparticle Enzyme Immunoassay, with an average intraassay coefficient of variation of 5%. Plasma immunoreactivities of C-peptide, glucagon, and pancreatic polypeptide (PP) were analyzed by commercially available radioimmunoassay kits (Biermann, Bad Nauheim, Germany and Euradiagnostica, The Netherlands [PP]). Immunoreactive (IR) GLP-1 was measured using the specific polyclonal antibody GA 1178 (Affinity Research, Nottingham, United Kingdom) as described previously [2]. The detection limit of the assay was 0.25 pmol/l. The antiserum did not crossreact with glucose-dependent insulinotropic peptide (GIP), pancreatic glucagon, glicentin, oxyntomodulin, or GLP-2. Intra- and inter-assay coefficients of variation were 3.4 and 10.4%, respectively. All values were expressed as mean±SEM.

Plasma and motility parameters were separately analyzed for each 60 min period. Pyloric tone was calculated as change from basal, the latter being determined as mean pyloric tone during the total basal period before starting the experiments. Differences of plasma hormones and glucose compared to the basal state were calculated as integrated values over basal (area under the response curve; AUC). Basal levels of plasma parameters were determined as the mean of the two basal values just before the start of each experiment. All samples were first tested for normality by the Kolmogoroff-Smirnoff test. Differences between experimental sets for each parameter were analysed by two-way repeated measures analysis of variance employing intravenous infusion and duodenal perfusion as factors. When this analysis indicated differences, a Student-Newman-Keuls multicomparison test was performed. Differences were considered significant at $P<0.05$.

Example 1

Motility Recordings and Blood Samples were Taken From Human Patients

Eleven healthy male volunteers, 23 to 28 years old and within 10% of ideal body weight, participated in the studies. None of them were taking medication, or suffering from gastrointestinal symptoms or systemic disease.

All studies were performed after an overnight fast. Two experiments were performed, separated by at least 1 week on subjects lying in a semirecumbent position. An indwelling catheter was inserted into an antecubital vein for intravenous infusions. A second catheter was inserted into a dorsal vein of the contralateral hand in a retrograde fashion for sampling of arterialized blood (Schirra et al. *Proc Assoc Am Physicians* 109, 84–97 (1997)).

Each experiment started after a basal period of at least 30 min, of which the last 15 min displayed a low motor activity (<5 antral contractions/10 min). On the interdigestive study day, 0.154 M saline was continuously perfused into the region of the lower duodenal flexure at a rate of 2.5 ml/min. In order to obtain physiological postprandial and supraphysiological plasma levels, a 60 min period of intravenous saline infusion was followed by two 60 min periods of intravenous infusion with GLP-1 at 0.4 and 1.2 pmol·kg$^{-1}$·min$^{-1}$ in the interdigestive experiments. During the initial 10 min of each infusion period, GLP-1 was infused at double doses (0.8 and 2.4 pmol·kg$^{-1}$·min$^{-1}$, respectively) to quickly establish steady state plasma levels. On the postprandial study day, the same intravenous infusions were administered with an intraduodenal lipid perfusion at 2.5 kcal/min (2.5 ml/min, Lipofundin MCT 10%, Braun Co., Melsungen, Germany). This lipid preparation consisted of 50% medium-chain triglycerides (MCT) and 50% long-chain triglycerides (LCT, soya bean oil). In the postprandial experiments, measurements continued for another 60 min with ongoing lipid perfusion after cessation of intravenous GLP-1.

Throughout the experiment, blood samples were taken immediately before the start of intravenous infusion, as well as in 10-min intervals thereafter. Blood was collected in ice-chilled EDTA tubes containing 1000 aprotinin (kallikrein inhibitory units/ml blood) and was centrifuged immediately. The plasma was stored at −20° C. until assayed.

Example 2

Motility Recordings of the Antro-pyloryo-duodenal Region

Perfusion manometry was recorded using a nine-lumen duodenal sleeve/side-hole catheter (Dentsleeve, South Australia, Australia). The manometric assembly incorporated a 4.5 cm long sleeve sensor, two antral side-holes (2 cm apart), and three duodenal side-holes (2 cm apart), beginning at the proximal and distal end of the sleeve, respectively. Two more side-holes were positioned across the sleeve spaced 1.5 cm apart. An additional lumen located 12 cm distal to the sleeve sensor was used for duodenal perfusion.

The correct position of the duodenal probe with the sleeve array straddling the pylorus was fluoroscopically checked before start of each experiment, and monitored throughout each study by measuring the transmucosal potential difference at the distal antral and the proximal duodenal port, as previously described (Schirra et al. *J Clin Invest* 97, 92–103 (1996)). A difference of at least −15 mV indicated correct transpyloric position of the tube.

The motility channels were perfused at a rate of 0.3 ml/min using a low-compliance pneumohydraulic pump (Arndorfer Medical Specialists, Greendale, Wis.). Pressures were measured by external transducers. Data were simultaneously recorded on the screen of a multichannel chart system (PC Polygraph, Synectics Medical, Stockholm, Sweden) and stored in the memory of a personal computer. Data were sampled and digitized at 8 Hz followed by digital smoothing by a factor of 2.

Example 3

Intravenous Infusion of GLP-1 Increases Plasma GLP-1 Levels

Intravenous infusion of GLP-1 dose-dependently increased plasma GLP-1 in the experiments with both duodenal saline and lipid reaching constant plasma levels within 20 min after start of infusion (FIG. 1, Table 3). Steady state plasma levels amounted to 6.2±0.6 pmol/l (low dose GLP-1) and 13.1±0.9 pmol/l (high dose GLP-1) with duodenal saline, and to 7.1±0.6 pmol/l (low dose GLP-1) and 14.4±0.9 pmol/l (high dose GLP-1) with duodenal lipid, respectively. Duodenal lipid slightly but significantly increased plasma GLP-1 compared to duodenal saline perfusion (2.4±0.3 pmol/l vs. 1.4±0.2 pmol/l, P<0.05). This difference remained constant with infusion of both loads of exogenous GLP-1. After cessation of GLP-1 during ongoing lipid perfusion, plasma GLP-1 immediately decreased and gradually returned to preinfusion values.

TABLE 1

Effect of physiological (low does, 0.4 pmol · kg$^{-1}$ · min$^{-1}$) and supraphysiological (high dose, 1.2 pmol · kg$^{-1}$ · min$^{-1}$) doses of GLP-1 on plasma glucose, and plasma immunoreactivities of GLP-1, insulin, glucagon, and pancreatic polypeptide with introduodenal perfusion of saline or lipid (2.5 kcal/min, 2.5 ml/min).

|  | GLP-1 (pmol/l · 60 min) | Plasma glucose (mmol/l · 60 min) | Insulin (mU/l · 60 min) | Glucagon (pg/ml · 60 min) | Pancreatic polypeptide (pg/ml · 60 min) |
|---|---|---|---|---|---|
| Intraduodenal Saline |  |  |  |  |  |
| Saline iv. | −0.8 ± 1.0 | 0.3 ± 0.1 | 1.5 ± 1.7 | 22.4 ± 16.2 | 10.8 ± 29.7 |
| GLP-1 iv.: low dose | 25.2 ± 2.6* | −2.3 ± 0.3* | 11.3 ± 2.4* | −59.0 ± 37.1* | −90.5 ± 32.7* |
| GLP-1 iv.: high dose | 67.4 ± 4.0*‡ | −2.5 ± 0.4* | 11.9 ± 5.1* | −68.6 ± 28.9* | −128.9 ± 33.2* |
| Intraduodenal Lipid |  |  |  |  |  |
| Saline iv. | 7.5 ± 1.7‖ | −1.2 ± 0.3‖ | 25.5 ± 4.4‖ | 145.9 ± 21.6‖ | 298.5 ± 66.9‖ |
| GLP-1 iv.: lose dose | 33.8 ± 2.9*‖ | −4.7 ± 0.5*‖ | 24.7 ± 4.8‖ | 99.7 ± 25.1*‖ | 7.7 ± 55.4*‖ |
| GLP-1 iv.: high dose | 75.2 ± 3.9*‡‖ | −4.5 ± 0.7*‖ | 31.4 ± 8.4‖ | 48.0 ± 33.8*‡‖ | −104.2 ± 71.1*‡ |
| Saline iv.: recovery | 17.1 ± 3.1*‡§ | −0.8 ± 0.6‡§ | 18.3 ± 2.7 | 189.0 ± 44.7‡§ | 294.4 ± 93.0‡§ |

Mean ± SEM of AUC over basal during each 60 min infusion period. N = 11. For the same intraduodenal perfusion: *: P < 0.05 vs. saline iv., ‡: P < 0.05 vs. low dose GLP-1, §: P < 0.05 vs. high dose GLP-1. For different intradoudenal perfusions: ‖: P < 0.05 vs. the same intravenous infusion/intraduodenal saline.

Example 4

GLP-1 Inhibits Antro-duodenal Motility

Transmucosal potential difference indicated correct transpyloric position of the probe during 95.9±1.6% and 92.5±2.0% of recording time with duodenal saline and lipid, respectively.

In the interdigestive experiments with duodenal saline perfusion, both dosages of GLP-1 significantly inhibited number, amplitudes, and motility indexes of contractions in the antrum and also in the duodenum (FIG. 2A, Table 1). The inhibition of antro-duodenal motility occurred within 2 min after starting the low dose of GLP-1. Within 20 min, the low dose GLP-1 nearly completely inhibited antro-duodenal motility. Even the low dose GLP-1 completely abolished the antral waves propagating across the pylorus to the duodenum over a distance of 4.5 cm and 6.5 cm, respectively (Table 2).

Compared to duodenal saline, duodenal lipid perfusion inhibited antral and duodenal contractility. Against a background of duodenal lipid, exogenous GLP-1 dose-dependently diminished number, amplitude, and motility indexes of antral and duodenal contractions to a residual level comparable to the interdigestive state (FIG. 2B, Table 1). With cessation of GLP-1, antro-duodenal motility immediately increased and returned to preinfusion activity. The duration of contractions remained unchanged with GLP-1 in all experiments.

TABLE 2

Effect of physiological (low does, 0.4 pmol · kg$^{-1}$ · min$^{-1}$) and
supraphysiological (high dose, 1.2 pmol · kg$^{-1}$ · min$^{-1}$) doses
of GLP-1 on antral and duodenal motility with intraduodenal perfusion of saline or lipid
(2.5 kcal/min, 2.5 ml/min).

|  | Antral Motility Contractions (number /) 60 min) | Motility Index (mmHg*s/60 min) | Amplitude (mmHg) | Duodenal Motility Contractions (number / 60 min) | Motility Index (mmHg*s/60 min) | Amplitude (mmHg) |
|---|---|---|---|---|---|---|
| Intraduodenal Saline | | | | | | |
| Saline iv. | 69.3 ± 9.9 | 18601 ± 5758 | 63.0 ± 7.5 | 183.7 ± 25.1 | 19502 ± 4321 | 39.5 ± 3.6 |
| GLP-1 iv.: lose dose | 12.6 ± 2.8* | 1478 ± 564* | 31.1 ± 3.1* | 36.0 ± 14.7* | 3447 ± 1624* | 25.0 ± 2.5* |
| GLP-1 iv.: high dose | 9.6 ± 2.8* | 957 ± 322* | 21.1 ± 3.1*‡ | 16.6 ± 3.9* | 1119 ± 226* | 17.5 ± 1.9*‡ |
| Intraduodenal Lipid | | | | | | |
| Saline iv. | 24.3 ± 4.5‖# | 2749 ± 695‖ | 32.5 ± 3.1‖ | 85.4 ± 16.4‖# | 9545 ± 2891‖# | 32.9 ± 3.1‖# |
| GLP-1 iv.: low dose | 12.1 ± 4.1* | 880 ± 351* | 23.6 ± 3.1* | 29.5 ± 5.8* | 2776 ± 890* | 26.0 ± 3.3* |
| GLP-1 iv.: high dose | 9.2 ± 2.9* | 628 ± 249* | 23.0 ± 2.7* | 16.6 ± 5.9*‡ | 1174 ± 499*‡ | 19.2 ± 3.1*‡ |
| Saline iv.: recovery | 28.7 ± 7.5‡§ | 3147 ± 785‡§ | 34.7 ± 3.8‡§ | 69.6 ± 21.2‡§ | 8732 ± 3574‡§ | 36.6 ± 4.5‡§ |

Mean ± SEM of actual values during each 60 min infusion period. Values for contractions and motility indices represent the sum of two antral and three duodenal side holes, respectively. N = 1. For the same intraduodenal perfusion: *: P < 0.05 vs. saline iv., ‡: P < 0.05 vs. low dose GLP-1, §: P < 0.05 vs. high dose GLP-1. For different intraduodenal perfusions: ‖: P < 0.05 vs. saline inv./intraduodenal saline, #: P < 0.05 vs. low dose GLP-1/ intraduodenal saline.

TABLE 3

Effect of physiological (low dose, 0.4 pmol · kg$^{-1}$ · min$^{-1}$)
and supraphysiological (high dose, 1.2 pmol · kg$^{-1}$ · min$^{-1}$) doses of GLP-
1 on pyloric motility and antro-pyloro-duodenal wave propagation with introduodenal
perfusion of saline or lipid (2.5 kcal/min, 2.5 ml/min).

|  | Pyloric Motility IPPW (number/10 min) | Pyloric tone (mmHg) | Antro-Pyloro-Duodenal Propagated Contractions (number/60 min) |
|---|---|---|---|
| Intraduodenal Saline | | | |
| Saline iv. | 1.6 ± 0.3 | 0.2 ± 0.5 | 9.8 ± 1.3 |
| GLP-1 iv.: lose dose | 10.1 ± 1.9* | 5.3 ± 0.9* | 0.0* |
| GLP-1 iv.: high dose | 8.6 ± 1.3* | 7.3 ± 1.5*‡ | 0.0* |
| Intraduodenal Lipid | | | |
| Saline iv. | 14.7 ± 1.5‖# | 3.1 ± 0.4‖# | — |
| GLP-1 iv.: low dose | 15.7 ± 2.5 | 7.4 ± 1.0*# | — |
| GLP-1 iv.: high dose | 15.5 ± 2.1 | 8.6 ± 1.0* | — |
| Saline iv.: recovery | 6.2 ± 1.1*‡§ | 5.1 ± 0.8*‡§ | — |

Mean ± SEM of actual values (IPPW) and of values over basal (tome) during each 60 min infusion period. N = 11. For the same intraduodenal perfusion: *: P <0.05 vs. Saline iv., ‡: P <0.05 vs. low dose GLP-1, §: P <0.05 vs. high dose GLP-1. For different intraduodenal perfusions: ‖: P <0.05 vs. saline iv./intraduodenal saline, #: P <0.05 vs. low dose GLP-1/ intraduodenal saline. IPPW: isolated pyloric pressure waves.

Example 5

GLP-1 Stimulates Pyloric Motility

Figure 3A:
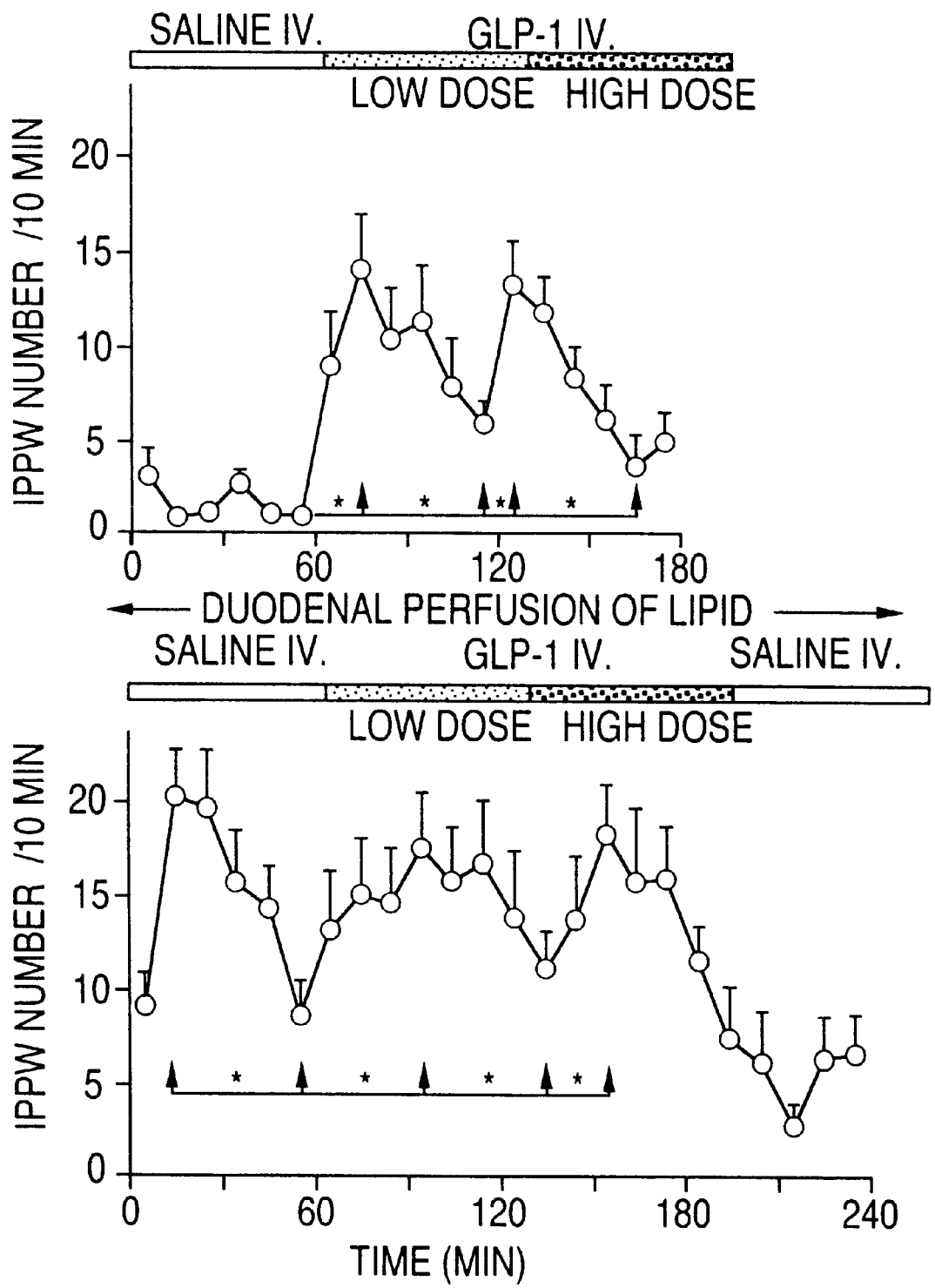
FIG. 3. Isolated pyloric pressure waves (A) and pyloric tone (B) in response to intravenous infusions of saline, GLP-1(7–36)amide at 0.4 and 1.2 pmol·kg$^{-1}$·min$^{-1}$ during concomitant duodenal perfusion of saline (upper panel) or lipid (2.5 kcal/min, lower panel) in eleven healthy volunteers. Mean±SEM. *:$p<0.05$ for comparison of time points indicated by arrows (paired t-test). For further statistical analysis, see Table 2.
Figure 3B:
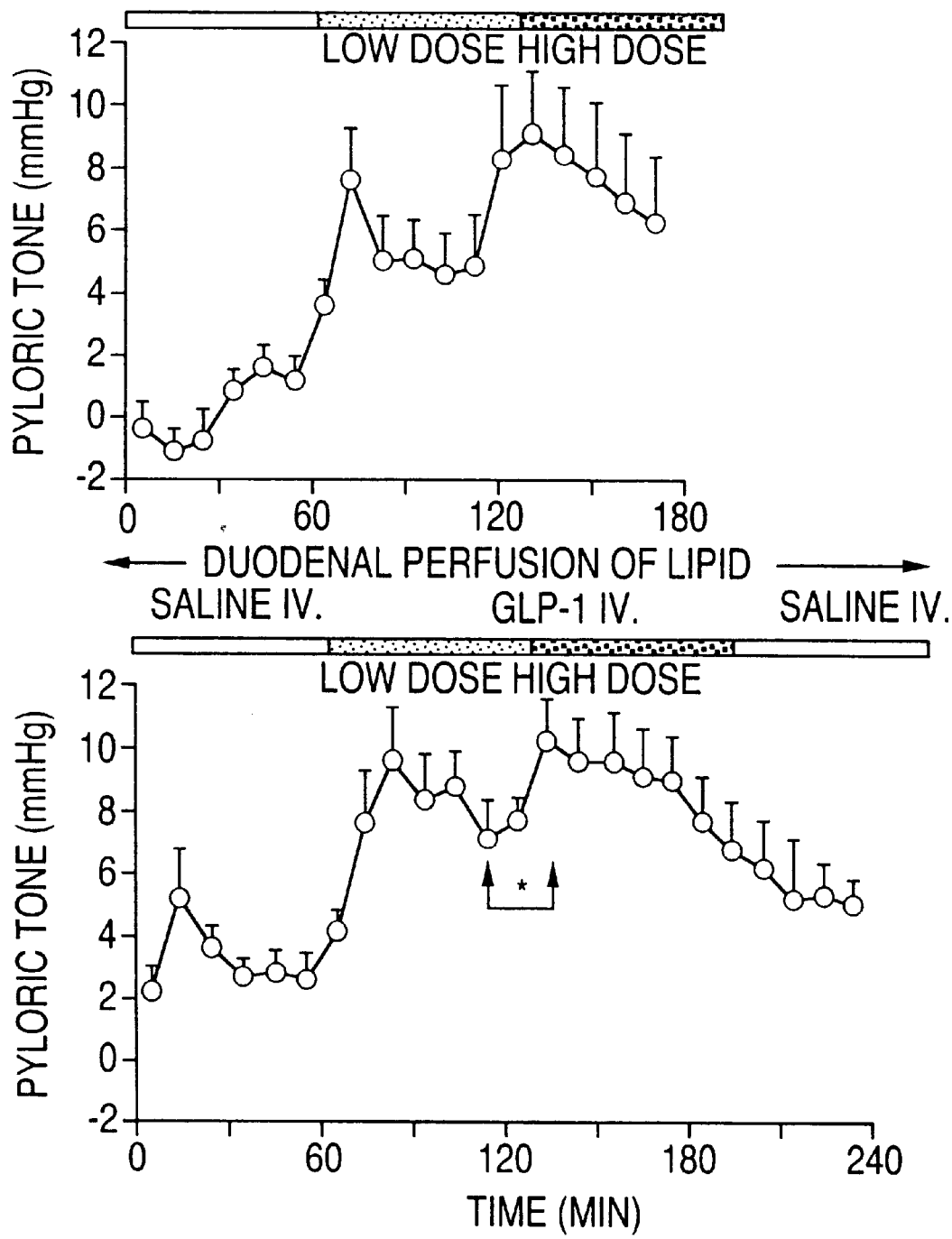
Figure 6A:
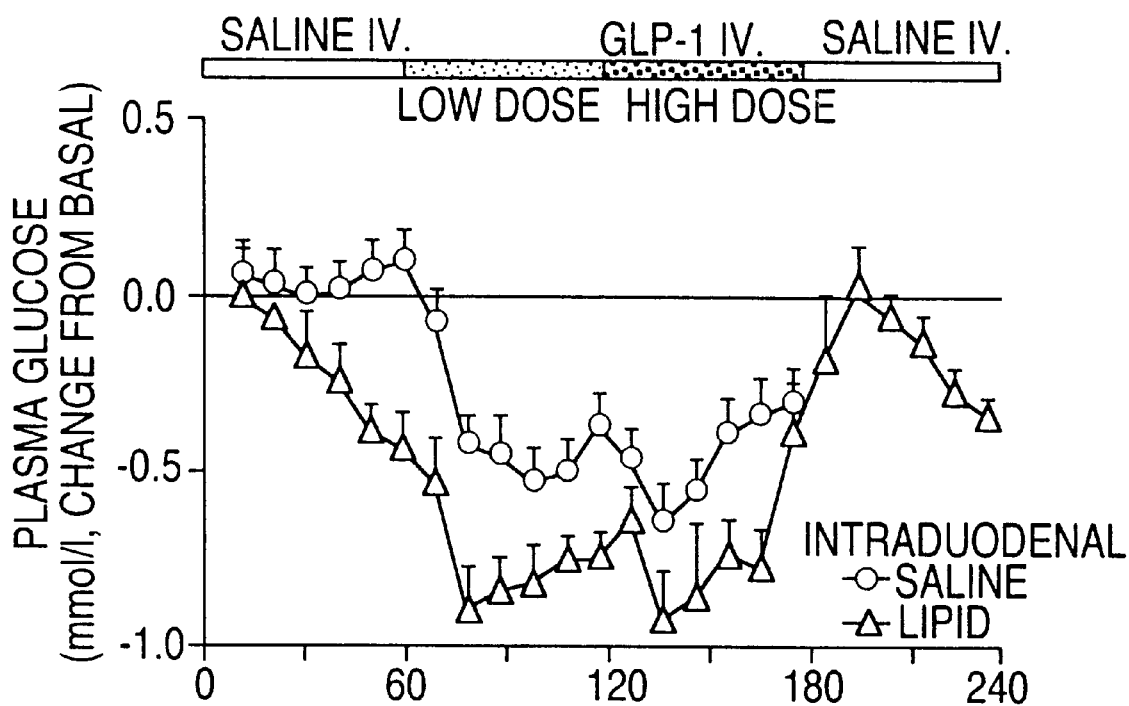
FIG. 6. Effects of intravenous infusions of saline, GLP-1(7–36)amide at 0.4 and 1.2 pmol·kg$^{1}$·min$^{-1}$ on plasma glucose (A) and immunoreactivities of glucagon (B), insulin (C), and pancreatic polypeptide (D) during concomitant duodenal perfusion of saline or lipid (2.5 kcal/min) in eleven healthy volunteers. Mean±SEM of incremental values over basal. For statistical analysis, see Table 3.
Figure 6C:
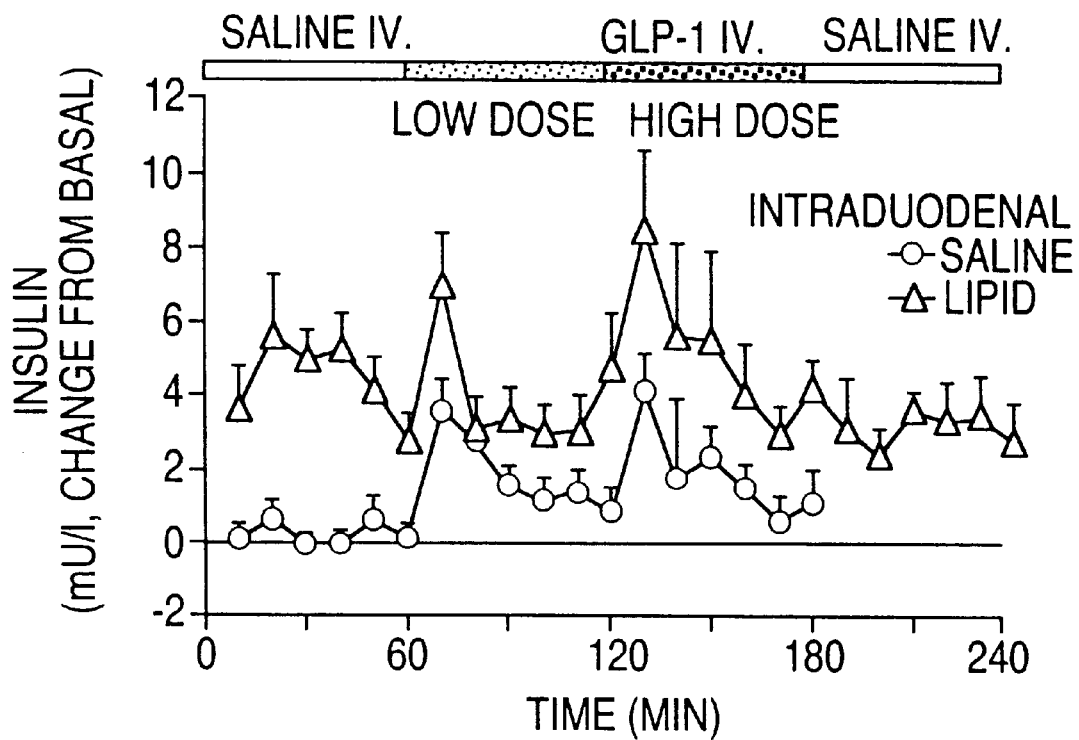

Pyloric tone increased in a dose-dependent fashion with exogenous GLP-1 in the interdigestive state (FIG. 3B, Table 2). Even with low dose GLP-1, the effect was significant within 10 min and fully established within 20 min after starting GLP-1 infusion. Pyloric tone stably increased with duodenal lipid when compared to duodenal saline, which was further enhanced by GLP-1 addition (FIG. 3B, Table 2). Pyloric tone steadily decreased after cessation of GLP-1, parallel to declining plasma levels. During the last 30 minutes of the experiment, pyloric tone was not significantly different from the first 60 min without GLP-1, indicating complete recovery (3.9±0.7 mmHg for the last 30 min vs. 3.1±0.4 mmHg during the first 60 min of the experiments, P=0.29).

IPPWs immediately and significantly increased with infusion of GLP-1 (FIG. 3A, Table 2). In contrast to the tonic pyloric response, however, increases of IPPWs were not dose-dependent and exhibited a fast increase followed by a marked decline. The latter phenomenon held true for both lipid alone and GLP-1 against a background of duodenal lipid. Stimulation of IPPW with duodenal lipid was significantly stronger than with GLP-1 alone, and duodenal lipid and exogenous GLP-1 did not act in an additive manner. Cessation of GLP-1 significantly decreased IPPWs compared to measurements in the initial 60 min without GLP-1.

GLP-1 triggered quickly duodenal phase III-like episodes in most of the volunteers in the interdigestive state. Duodenal phase III-like activity has been previously demonstrated in response to a variety of stimuli such as intraduodenal infusion of dextrose (Heddle et al., *Gut* 29, 1349–57 (1988)) and lipid (Heddle et al., *Am J Physiol* 254, G671–9 (1988)), intravenous β-endorphin (Camilleri et al., *Am J Physiol* 25 1, G147–54 (1986)), during stress induced by cold (Fone et al., *Gastroenterol.* 98, 1155–61 (1990)), pain (Thompson et al., *Gastroenterol.* 83, 1200–6 (1982)), or labyrinthine stimulation (Stanghellini et al., *Gastroenterol.* 85, 83–91 (1983)), and acute hyperglycaemia (Fraser ET AL., *Gut* 32, 475–8 (1991)). Interestingly, intraduodenal lipid stimulated duodenal phase III-like episodes in the present study. However, GLP-1 infusion in conjunction with lipid perfusion was accompanied by duodenal phases III in only two out of 11 subjects. All duodenal phase III-like episodes strongly paralleled the initiation of pyloric stimulation, either by GLP-1 or by duodenal lipid. Therefore, the initial phasic and transient stimulation of the duodenum may originate in the pylorus, and, although its functional significance is still uncertain, it may indicate a rather unspecific reaction in response to a strong stimulation of the pyloric muscle by GLP-1 or lipid. Initiation of phasic and tonic stimulation of the pylorus was almost paralleled by duodenal phases III with both doses of GLP-1 in the interdigestive state, occurring within 10 min after GLP-1 infusion (FIG. 4). These duodenal phases III were demonstrated in seven out of 11 volunteers after the low dose of GLP-1, and in five volunteers after the high dose of GLP-1. Seven out of 11 volunteers immediately developed a duodenal phase III in parallel with pyloric stimulation after intraduodenal lipid infusion. The typical pattern of the antro-pyloro-duodenal motility seen with GLP-1 infusion is shown in FIG. 5.

Example 6

GLP-1 Decreases Plasma Glucose

In the interdigestive experiments, basal plasma glucose levels were 4.3±0.1 mmol/l and significantly dropped with both doses of GLP-1 (FIG. 5A, Table 3). Plasma glucose levels decreased slightly compared to duodenal saline perfusion with duodenal lipid. This decrease was further pronounced with both doses of GLP-1, followed by a significant increase after cessation of GLP-1. However, nadir of plasma glucose amounted to 3.58±0.12 mmol/l and 3.64±0.14 mmol/l at 20 min each with low and high doses of GLP-1, respectively. These nadir values do not represent hypoglycemia.

Basal plasma levels of insulin averaged 6.0±0.7 mU/l and 6.1±0.7 mU/l before start of duodenal saline and lipid infusion, respectively. Both doses of GLP-1 led to a short, initial rise of insulin, followed by a decline (FIG. 5C). Compared to duodenal saline, duodenal lipid elicited a small, but significant increase in plasma insulin, which was maintained throughout each study (Table 3).

Basal levels of glucagon amounted to 91.5±8.8 pg/ml and 88.2±8.6 pg/ml in the studies with duodenal saline and lipid, respectively (difference not significant). With duodenal saline and lipid, GLP-1 significantly and dose-dependently diminished plasma glucagon (FIG. 5B). Plasma glucagon then immediately increased with cessation of GLP-1 in the lipid experiments. Compared to saline perfusion, duodenal lipid significantly raised glucagon, which then remained elevated throughout the experiments (Table 3).

Example 7

GLP-1 Dose-dependently Decreases Pancreatic Polypeptide Levels

The inhibition of pancreatic polypeptide (PP), a hormone of the endocrine pancreas, is under strong vagal cholinergic control. PP is inhibited in humans with subcutaneous and intravenous GLP-1 after oral meal ingestion (Schirra et al. *J. Endocrinol*, 156, 177–86 (1998); Schirra et al. *Proc Assoc Am Physicians* 109, 84–97 (1997); Dupre et al. *Diabetes* 44, 626–30 (1995)). Intestinal stimulation of PP release requires stimulation of enteropancreatic cholinergic reflexes by duodenal delivery of nutrients (Schwartz, *Gastroenterol.* 85, 1411–25 (1983)), and a reduced duodenal nutrient load during retarded gastric emptying would explain this PP response. In the results marshaled by the inventor, PP release triggered by lipid perfusion directly into the duodenum dose-dependently decreased with GLP-1 infusion, followed by a prompt and complete recovery after cessation of GLP-1 treatment. Moreover, in the interdigestive studies, PP was significantly reduced below basal levels. Therefore, the present inventor finds that GLP-1 inhibits efferent vagal-cholinergic activity, thereby diminishing PP release and at least partially contributing to the inhibition of antral and duodenal motility via a central pathway. Receptors for GLP-1 are present in circumventricular organs like the subfornical organ, the nucleus of the solitary tract and the area postrema (Göke et al., *Eur. J. Neurosci* 7, 2294–2300 (1995)). In addition, it has been recently shown in rat that GLP-1 induced inhibition of gastric emptying involves a capsaicin-sensitive pathway indicating an interaction with vagal afferent nerves (Imeryuz et al., *Am. J. Physiol.* 273, G920–7 (1997)). A direct action of GLP-1 on pancreatic PP cells or a paracrine effect via somatostatin seems unlikely because GLP-1 induces stimulation, instead of inhibition of PP release from isolated human pancreatic islets (Fehmann et al., *Pancreas* 11, 196–200 (1995)).

Basal levels of pancreatic polypeptide averaged 64.3±8.6 pg/ml and 71.9±8.7 pg/ml before start of duodenal saline and lipid, respectively (P=0.32). With duodenal lipid, levels of pancreatic polypeptide markedly rose when compared to saline perfusion (FIG. 5D, table 3). Intravenous GLP-1 dose-dependently diminished pancreatic polypeptide with and without duodenal lipid, and pancreatic polypeptide was significantly reduced below basal levels in the experiments with duodenal saline. After cessation of GLP-1, an instantaneous increase of pancreatic polypeptide levels was observed in the studies with duodenal lipid perfusion, indicating a complete recovery.

What is claimed is:

1. A method of inhibiting antro-duodenal motility in a patient in need thereof, which comprises parenterally administering to the patient a therapeutically effective amount of GLP-1(7–36)amide, in a dose of from about 0.4–1.2 pmol/kg/min.

2. The method of claim 1 whereby the GLP-1(7–36)amide is administered in combination with another antimotility agent.

3. A method of inhibiting antro-duodenal motility in a patient in need thereof, which comprises intravenously administering to the patient a therapeutically effective amount of GLP-1(7–36)amide in a dose of about 0.4 pmol/kg/min.

4. A method of inhibiting antro-duodenal motility in a patient in need thereof, which comprises intravenously administering to the patient a therapeutically effective amount of GLP-1(7–36)amide, in a dose of about 0.4 pmol/kg/min, and further providing that the GLP1(7–36)amide is administered in combination with another antimotility agent.

5. A method of reducing antro-duodenal motility in a patient in need thereof, which comprises intravenously administering to the patient a therapeutically effective amount of GLP-1(7–36)amide, in a dose of from about 0.4–1.2 pmol/kg/min, whereby the antral motility in the patient is reduced to 12.6±2.8 or less, and the duodenal motility in the patient is reduced to 36.0±14.7 or less.

* * * * *

SEQUENCE LISTING

<160> NUMBER OF SEQ ID NOS: 13

<210> SEQ ID NO 1
<211> LENGTH: 37
<212> TYPE: PRT
<213> ORGANISM: Unknown Organism
<220> FEATURE:
<223> OTHER INFORMATION: Description of Unknown Organism: Mammalian GLP
      peptide

<400> SEQUENCE: 1

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 36
<212> TYPE: PRT
<213> ORGANISM: Unknown Organism
<220> FEATURE:
<223> OTHER INFORMATION: Description of Unknown Organism: Mammalian GLP
      peptide

<400> SEQUENCE: 2

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg
        35

<210> SEQ ID NO 3
<211> LENGTH: 31
<212> TYPE: PRT
<213> ORGANISM: Unknown Organism
<220> FEATURE:
<223> OTHER INFORMATION: Description of Unknown Organism: Mammalian GLP
      peptide

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Unknown Organism
<220> FEATURE:
<223> OTHER INFORMATION: Description of Unknown Organism: Mammalian GLP
      peptide

<400> SEQUENCE: 4

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

```
<210> SEQ ID NO 5
<211> LENGTH: 29
<212> TYPE: PRT
<213> ORGANISM: Unknown Organism
<220> FEATURE:
<223> OTHER INFORMATION: Description of Unknown Organism: Truncated form
      of GLP-1

<400> SEQUENCE: 5

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg Gly
            20                  25

<210> SEQ ID NO 6
<211> LENGTH: 28
<212> TYPE: PRT
<213> ORGANISM: Unknown Organism
<220> FEATURE:
<223> OTHER INFORMATION: Description of Unknown Organism: Truncated form
      of GLP-1

<400> SEQUENCE: 6

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg
            20                  25

<210> SEQ ID NO 7
<211> LENGTH: 39
<212> TYPE: PRT
<213> ORGANISM: Unknown Organism
<220> FEATURE:
<223> OTHER INFORMATION: Description of Unknown Organism: Exendrin 3

<400> SEQUENCE: 7

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 8
<211> LENGTH: 31
<212> TYPE: PRT
<213> ORGANISM: Unknown Organism
<220> FEATURE:
<223> OTHER INFORMATION: Description of Unknown Organism: Exendrin 4
      (9-39(NH2)

<400> SEQUENCE: 8

Asp Leu Ser Lys Gln Met Glu Glu Glu Ala Val Arg Leu Phe Ile Glu
 1               5                  10                  15

Trp Leu Lys Asn Gly Gly Pro Ser Ser Gly Ala Pro Pro Pro Ser
            20                  25                  30

<210> SEQ ID NO 9
<211> LENGTH: 39
<212> TYPE: PRT
<213> ORGANISM: Unknown Organism
<220> FEATURE:
<223> OTHER INFORMATION: Description of Unknown Organism: Exendrin 4

<400> SEQUENCE: 9
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
            35

<210> SEQ ID NO 10
<211> LENGTH: 38
<212> TYPE: PRT
<213> ORGANISM: Unknown Organism
<220> FEATURE:
<223> OTHER INFORMATION: Description of Unknown Organism: Helospectin I

<400> SEQUENCE: 10

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser Ser
            35

<210> SEQ ID NO 11
<211> LENGTH: 37
<212> TYPE: PRT
<213> ORGANISM: Unknown Organism
<220> FEATURE:
<223> OTHER INFORMATION: Description of Unknown Organism: Helospectin II

<400> SEQUENCE: 11

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser
            35

<210> SEQ ID NO 12
<211> LENGTH: 35
<212> TYPE: PRT
<213> ORGANISM: Unknown Organism
<220> FEATURE:
<223> OTHER INFORMATION: Description of Unknown Organism: Helodermin

<400> SEQUENCE: 12

His Ser Asp Ala Ile Phe Thr Glu Glu Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35

<210> SEQ ID NO 13
<211> LENGTH: 35
<212> TYPE: PRT
<213> ORGANISM: Unknown Organism
<220> FEATURE:
<223> OTHER INFORMATION: Description of Unknown Organism: Q8, Q9 heliodermin

```
<400> SEQUENCE: 13

His Ser Asp Ala Ile Phe Thr Gln Gln Tyr Ser Lys Leu Leu Ala Lys
 1               5                  10                  15

Leu Ala Leu Gln Lys Tyr Leu Ala Ser Ile Leu Gly Ser Arg Thr Ser
                20                  25                  30

Pro Pro Pro
        35
```